United States Patent
Matsumoto

(10) Patent No.: US 9,117,289 B2
(45) Date of Patent: Aug. 25, 2015

(54) MEDICAL IMAGING SYSTEM, MEDICAL IMAGE PROCESSING APPARATUS, AND COMPUTER-READABLE MEDIUM

(71) Applicant: KONICA MINOLTA, INC., Tokyo (JP)

(72) Inventor: Hiroaki Matsumoto, Yokohama (JP)

(73) Assignee: KONICA MINOLTA, INC. (JP)

( * ) Notice: Subject to any disclaimer, the term of this patent is extended or adjusted under 35 U.S.C. 154(b) by 179 days.

(21) Appl. No.: 13/668,694

(22) Filed: Nov. 5, 2012

(65) Prior Publication Data
US 2013/0121556 A1    May 16, 2013

(30) Foreign Application Priority Data

Nov. 11, 2011    (JP) ................................ 2011-247358
Nov. 11, 2011    (JP) ................................ 2011-247361

(51) Int. Cl.
*G06K 9/00* (2006.01)
*G06T 7/20* (2006.01)
*G06T 7/00* (2006.01)
*A61B 6/00* (2006.01)

(52) U.S. Cl.
CPC ............... *G06T 7/2033* (2013.01); *A61B 6/50* (2013.01); *A61B 6/5264* (2013.01); *G06T 7/0012* (2013.01); *G06T 2207/10116* (2013.01); *G06T 2207/30061* (2013.01)

(58) Field of Classification Search
None
See application file for complete search history.

(56) References Cited

U.S. PATENT DOCUMENTS

| | | | | |
|---|---|---|---|---|
| 8,610,803 | B2 * | 12/2013 | Omi et al. ...................... | 348/246 |
| 2004/0179651 | A1 * | 9/2004 | Tong et al. ................... | 378/98.8 |
| 2006/0274145 | A1 * | 12/2006 | Reiner ............................ | 348/62 |
| 2007/0071171 | A1 * | 3/2007 | Hayashida et al. ............. | 378/98 |
| 2009/0041305 | A1 * | 2/2009 | Luo et al. ...................... | 382/107 |
| 2010/0086189 | A1 * | 4/2010 | Wang et al. ................... | 382/132 |
| 2011/0246521 | A1 * | 10/2011 | Luo et al. ..................... | 707/776 |

(Continued)

FOREIGN PATENT DOCUMENTS

| | | | |
|---|---|---|---|
| JP | 4-364834 | A | 12/1992 |
| JP | 2006-376 | A | 1/2006 |
| JP | 2006-000376 | * | 5/2006 |
| JP | 2010-214057 | A | 9/2010 |

OTHER PUBLICATIONS

Chen et al. Development and evaluation of a computer-aided diagnostic scheme for lung nodule detection in chest radiographs by means of two-stage nodule enhancement with support vector classification, Med. Phys. vol. 38 (4), Apr. 2011, pp. 1844-1858.*

Luo et al. "Motion blur detection in radiographs," Medical Imaging 2008, Proc. of SPIE vol. 6914, pp. 1-8.*

*Primary Examiner* — Vu Le
*Assistant Examiner* — Samah Beg
(74) *Attorney, Agent, or Firm* — Cantor Colburn LLP

(57) ABSTRACT

A medical imaging system includes: an image generating unit which captures an image of a subject and generates a medical image which is a still image; a region extracting unit which extracts a subject region from the medical image and extracts a local region which includes no edge from the subject region; a motion judging unit which extracts high spatial frequency components from the local region extracted by the region extracting unit and judges whether there is any motion in the subject during image capture based on the extracted high spatial frequency components; and a controlling unit which causes an outputting unit to output a judgment result made by the motion judging unit.

9 Claims, 25 Drawing Sheets

(56) References Cited

U.S. PATENT DOCUMENTS

| | | | |
|---|---|---|---|
| 2012/0093399 A1* | 4/2012 | Paik et al. | 382/164 |
| 2012/0201426 A1* | 8/2012 | Jasinski et al. | 382/107 |
| 2012/0201427 A1* | 8/2012 | Jasinski et al. | 382/107 |
| 2013/0156267 A1* | 6/2013 | Muraoka et al. | 382/103 |
| 2014/0140479 A1* | 5/2014 | Wang et al. | 378/62 |

* cited by examiner

HORIZONTAL SPATIAL FREQUENCY

CANDIDATE REGION FOR ENLARGEMENT

REGION FOR ENLARGEMENT

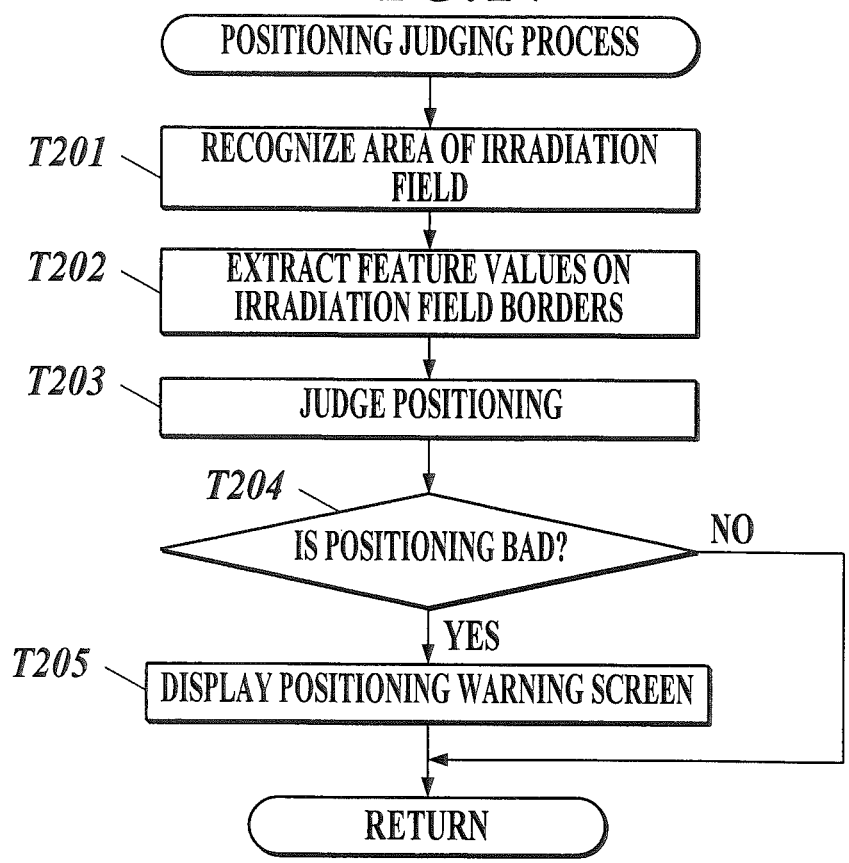

MEDICAL IMAGING SYSTEM, MEDICAL IMAGE PROCESSING APPARATUS, AND COMPUTER-READABLE MEDIUM

CROSS-REFERENCE TO RELATED APPLICATION

The present U.S. patent application claims a priority under the Paris Convention of Japanese patent application Nos. 2011-247358 and 2011-247361 both filed on Nov. 11, 2011 which shall be a basis of correction of an incorrect translation, and is incorporated by reference herein.

BACKGROUND OF THE INVENTION

1. Field of the Invention

The present invention relates to a medical imaging system, a medical image processing apparatus, and a computer-readable medium.

2. Description of the Related Art

In recent years, digital still images are generated for medical purposes by capturing images of diagnostic regions as subjects, and image diagnosis is done based on such medical images generated.

When there are motions in a subject while capturing a medical image, a subject blur happens in the medical image and motion artifacts are caused as slight burring of the human anatomy is imaged. Since an image that includes motion artifacts is not appropriate for diagnostic use, such medical image having motion artifacts requires a retake.

Therefore, for example, Patent Literature 1 (the publication of Japanese Patent No. 4539186) disclosed a technology in which it is judged whether there are motions in a subject while capturing a still image for medical purposes, and a medical image including motion artifacts is thus prevented from being used for diagnosis and efficiency of imaging operations is improved. In this Patent Literature 1, high spatial frequency components in the medical image are extracted, and existence of motions is judged based on the high spatial frequency components extracted.

Incidentally, in a case of a medical image of the front chest in which the lung field is captured as a subject, motion artifacts may happen due to breathing motions during radiation exposure for radiography. In such a case, the rib bones of the subject are imaged while remaining still, and motion artifacts happen in the blood vessels in the lung field of the subject.

In order to judge existence of motions in this kind of medical image, it is required to extract high spatial frequency components of the blood vessel regions in the lung field where motion artifacts happen. At this time, if edges of the rib bones are included in the regions where the high spatial frequency components are extracted, a problem arises that existence of motions cannot be judged correctly based on the extracted high spatial frequency components because the edges contain a number of high spatial frequency components.

SUMMARY OF THE INVENTION

An object of the present invention is to be able to accurately judge whether there is a motion in a subject while capturing a still image for medical purposes.

To achieve at least one of the abovementioned objects, a medical imaging system, reflecting one aspect of the present invention, includes:

an image generating unit which captures an image of a subject and generates a medical image which is a still image;

a region extracting unit which extracts a subject region from the medical image and extracts a local region which includes no edge from the subject region;

a motion judging unit which extracts high spatial frequency components from the local region extracted by the region extracting unit and judges whether there is any motion in the subject during image capture based on the extracted high spatial frequency components; and a controlling unit which causes an outputting unit to output a judgment result made by the motion judging unit.

Preferably, the region extracting unit divides the subject region into a plurality of small regions and extracts a plurality of local regions which include no edge from the plurality of small regions, and the motion judging unit extracts high spatial frequency components from each of the plurality of local regions extracted by the region extracting unit, and judges whether there is any motion in the subject during image capture based on the high spatial frequency components extracted from the plurality of local regions.

Preferably, the motion judging unit extracts high spatial frequency components for a plurality of directions and judges whether there is any motion in the subject during image capture based on the extracted high spatial frequency components for the plurality of directions.

Preferably, the medical imaging system further includes:

a preview image generating unit which generates a preview image by reducing the medical image; and a display unit which displays the preview image, wherein the region extracting unit extracts a subject region from the preview image and extracts the local region which includes no edge from the subject region, wherein the motion judging unit extracts high spatial frequency components from the local region extracted from the preview image, and judges whether there is any motion in the subject in the medical image based on the extracted high spatial frequency components, and wherein the controlling unit causes the display unit to display a warning when it is judged by the motion judging unit that there is a motion in the subject in the medical image.

Preferably, the medical imaging system further includes:

a preview image generating unit which generates a preview image by reducing the medical image;

a display unit which displays the preview image; and an image processing unit which executes image processing on the preview image, wherein the region extracting unit extracts a subject region from a preview image which has been undergone the image processing executed by the image processing unit and extracts the local region which includes no edge from the subject region, wherein the motion judging unit extracts high spatial frequency components from the local region extracted from the preview image which has been undergone the image processing executed by the image processing unit, and judges whether there is any motion in the subject in the medical image based on the extracted high spatial frequency components, and wherein the controlling unit causes the display unit to display a warning when it is judged by the motion judging unit that there is a motion in the subject in the medical image.

To achieve at least one of the abovementioned objects, a medical image processing apparatus, reflecting another aspect of the present invention, includes:

a region extracting unit which extracts a subject region from a medical image which is a still image obtained by imaging a subject, and extracts a local region which includes no high spatial frequency component due to an edge from the subject region;

a motion judging unit which extracts high spatial frequency components from the local region extracted by the region extracting unit and judges whether there is a motion in the subject during image capture based on the extracted high spatial frequency components; and a controlling unit which causes an outputting unit to output a judgment result made by the motion judging unit.

To achieve at least one of the abovementioned objects, a computer-readable medium, reflecting still another aspect of the present invention, makes a computer to function as:

a region extracting unit which extracts a subject region from a medical image which is a still image obtained by imaging a subject, and extracts a local region which includes no high spatial frequency component due to an edge from the subject region;

a motion judging unit which extracts high spatial frequency components from the local region extracted by the region extracting unit and judges whether there is a motion in the subject based on the extracted high spatial frequency components; and a controlling unit which causes an outputting unit to output a judgment result made by the motion judging unit.

BRIEF DESCRIPTION OF THE DRAWINGS

The present invention will be more fully understood by the following detailed description and the accompanying drawings. However, these are not intended to limit the present invention, wherein:

FIG. 17 is a flowchart showing a positioning judging process which is an example of an image judging process executed at step T9 shown in FIG. 16;

PREFERRED EMBODIMENTS OF THE PRESENT INVENTION

Embodiments of a medical imaging system according to the present invention will be described below with reference to the drawings. It should be noted, however, that the scope of the invention is not limited to the illustrated examples.

[First Embodiment]

First of all, the first embodiment of the present invention will be explained.

(Configuration of the Medical Imaging System)

First, the configuration of the medical imaging system 100 of this embodiment will be described.

Figure 1:
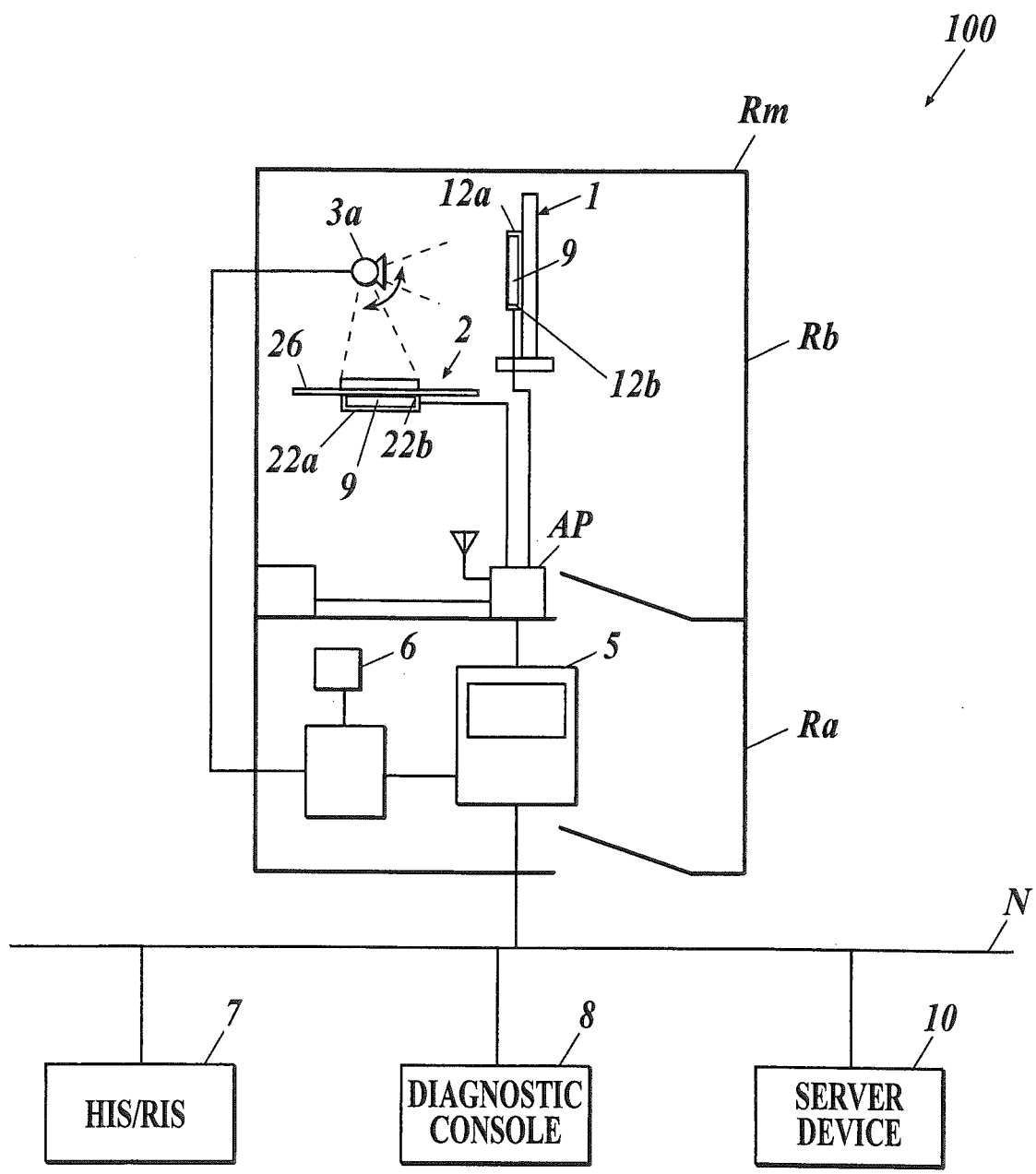
FIG. 1 is a view showing the whole configuration of a medical imaging system according to a first embodiment.

FIG. 1 is a view showing an example of the whole configuration of the medical imaging system 100 according to the embodiment of the present invention. The medical imaging system 100 is a system which captures a still image of a part of a patient's body (specifically, imaging region of the patient) as a subject, by performing radioactive irradiation of the subject. FIG. 1 shows a case where the medical imaging system 100 is constructed in a radiography room Rm.

The radiography room Rm is provided with, for example, a bucky device for radiography in a standing position 1, a bucky device for radiography in a decubitus position 2, a radiation source 3, an imaging console 5, an operating station 6, and an access point AP. There are a front room Ra and an imaging room Rb provided in the radiography room Rm. Since the imaging console 5 and the operating station 6 are provided in the front room Ra, radiation exposure to an operator such as a radiographer is prevented.

Next, each device in the radiography room Rm will be explained.

The bucky device 1 is a device which holds a FPD (flat panel detector) 9 for image capture at a standing position. The bucky device 1 includes a holding part 12*a* for holding the FPD 9, and a connector 12*b* to which a connector of the FPD 9 mounted on the holding part 12*a* is connected. The connector 12*b* transmits and receives data to and from the FPD 9 which is mounted onto the holding part 12*a*, and supplies power to the FPD 9. In addition, the bucky device 1 is provided with an interface which transmits/receives data to/from external devices such as the imaging console 5 through a communication cable via the access point AP, and a foot switch which moves the holding part 12*a* in the vertical or horizontal direction.

The bucky device 2 is a device which holds the FPD 9 for image capture in a decubitus position. The bucky device 2 includes a holding part 22*a* for holding the FPD 9, and a connector 22*b* to which a connector of the FPD 9 mounted on the holding part 22*a* is connected. The connector 22*b* transmits and receives data to and from the FPD 9 mounted on the holding part 22*a*, and supplies power to the FPD 9. In addition, the bucky device 2 is provided with an interface which transmits/receives data to/from external devices such as the imaging console 5 through a communication cable via the access point AP, and a subject stand 26 on which the subject is mounted.

The radiation source 3 is, for example, hung from the ceiling of the radiography room Rm. At the time of imaging, the radiation source 3 is activated based on an instruction from the imaging console 5, and is adjusted to predetermined position and orientation by driving mechanism which is not illustrated. Then, by changing the direction of radioactive irradiation, the radiation source 3 is able to emit radiation (X ray) to the FPD 9 which is mounted onto the bucky device for radiography in a standing position 1 or the bucky device for radiography in a decubitus position 2. Moreover, the radiation source 3 emits radiation once in accordance with the instruction of radioactive irradiation transmitted from the operating station 6 to capture a still image.

The imaging console 5 is a medical image processing device which controls imaging by controlling the radiation source 3 and the FPD 9, performs image processing on a medical image which has been generated by image capture, and displays the image for confirmation. The imaging console 5 is connected to a HIS/RIS (hospital information system/radiology information system) 7, a diagnostic console 8, a server device 10, and so on via a LAN (local area network), and controls the radiation source 3 and the FPD 9 to activate the same to conduct image capture based on imaging order information transmitted from the HIS/RIS 7.

Figure 2:
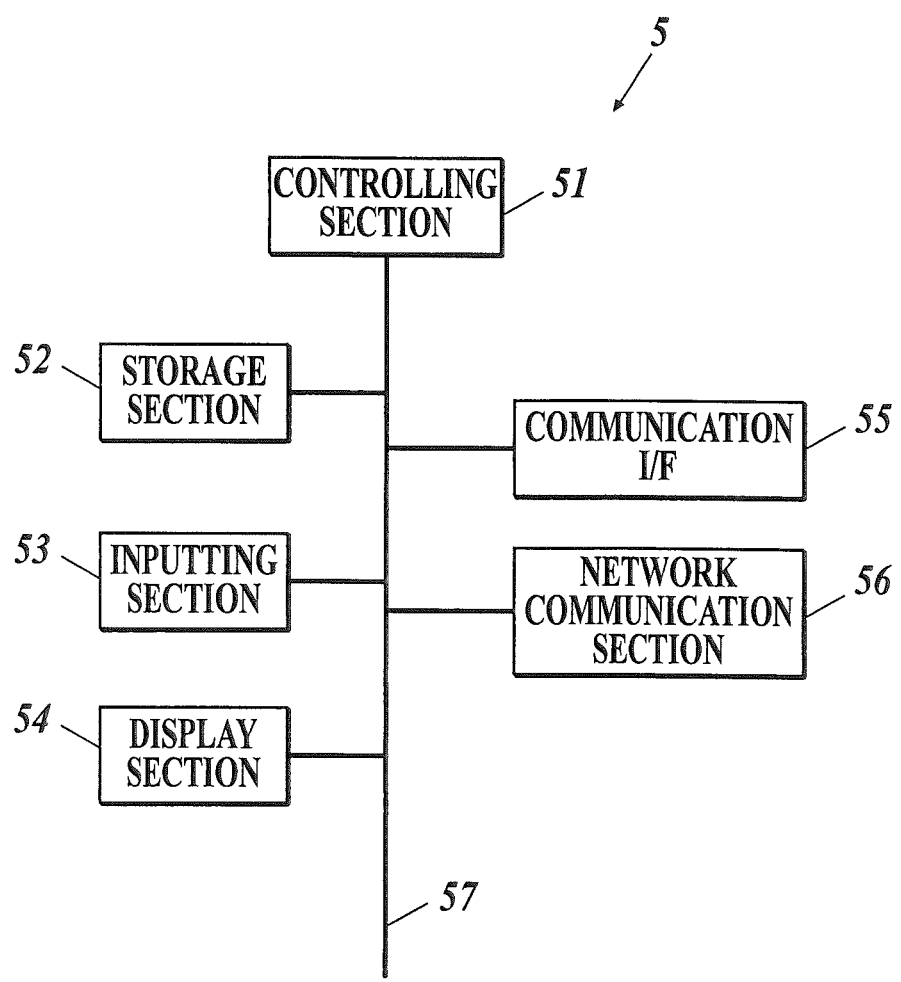
FIG. 2 is a block diagram showing the functional configuration of an imaging console.

FIG. 2 shows a configuration example of a main part of the imaging console 5. As illustrated in FIG. 2, the imaging console 5 is constructed by a controlling section 51, a storage section 52, an inputting section 53, a display section 54, a communication I/F 55, a network communication section 56 and so on, and each of these sections is connected to each other by a bus 57.

The controlling section 51 is configured by a CPU, a RAM and the like. The CPU of the controlling section 51 reads out various programs such as system programs and process programs stored in the storage section 52, expands these programs in the RAM, and executes various processes according to the expanded programs.

For instance, the controlling section 51 makes an inquiry to the HIS/RIS 7 through the network communication section 56 in every predetermined period, and obtains imaging order information which is newly registered in the HIS/RIS 7.

Further, for example, the controlling section 51 executes a later-described imaging controlling process, and the imaging console 5 controls the radiation source 3 and the FPD 9 to conduct image capture based on the imaging order information which was obtained from the HIS/RIS 7. Then, the controlling section 51 extracts local regions which do not contain any edge from a subject region of a medical image obtained from the image capture. The controlling section 51 then judges whether there was any motion of the subject during the image capture based on the high spatial frequency components extracted from the local regions extracted, and displays the judgment result on the display section 54. In other words, the controlling section 51 realizes functions as a region extracting unit, a motion judging unit, and a controlling unit.

The storage section 52 is configured by, for example, an HDD (hard disk drive), a semiconductor non-volatile memory, or the like.

The storage section 52 stores various programs and data.

For example, the storage section 52 stores various programs for executing the above-mentioned imaging controlling process, as well as image processing parameters (a lookup table which defines a gradation curve used for gradation processing, enhancements in frequency processing) for adjusting the image data of the medical image to have an appropriate image quality for diagnosis of each region.

Moreover, imaging conditions (radioactive irradiation conditions and image readout conditions) are stored in the storage section 52 in correspondence with imaged regions, respectively. The radioactive irradiation conditions include, for example, a value of X-ray tube current, a value of X-ray tube voltage, a kind of filter, and a SID (source to image-receptor distance).

In addition, the storage section 52 stores characteristic information of the FPD 9. Here, the characteristic information means characteristics of detection elements and a scintillator panel of the FPD 9.

Further, the storage section 52 stores the imaging order information which is transmitted from the HIS/RIS 7 in every given period.

The inputting section 53 is configured by a keyboard which includes character input keys, number input keys, and various function keys, and a pointing device such as a mouse. The inputting section 53 outputs a keypress signal from a key which is pressed on the keyboard, and an operation signal from the mouse to the controlling section 51 as input signals.

The display section 54 is structured by, for example, a monitor such as CRT (cathode ray tube) and a LCD (liquid crystal display), and displays various screens in accordance with instructions of display signals inputted from the controlling section 51.

Alternatively, a pressure-sensitive (resistance film pressure type) touch panel (not shown) having transparent electrodes arrayed in a grid-like shape may be formed on the screen of the display section 54 so that a touch screen is obtained where the display section 54 and the inputting section 53 are configured in an integral fashion. In this case, the touch panel is configured so that XY coordinates of a point touched by the human finger or a touch pen is detected, and the detected position signal is outputted to the controlling section 51 as an operation signal. Alternatively, the display part 54 may have higher definition than a monitor which is used for a normal PC (personal computer).

The communication I/F 55 is an interface which is connected to the bucky device 1, the bucky device 2, the radiation source 3, the FPD 9, through the access point AP, and transmits/receives data wirelessly or through a cable to/from them. In this embodiment, the communication I/F 55 transmits a polling signal to the FPD 9 through the access point AP as necessary.

The network communication section 56 is configured by a network interface or the like, and transmits/receives data to/from external devices connected to a communication network N through the switching hub.

The operating station 6 is an input device which is connected to the radiation source in the radiography room and inputs radioactive irradiation instructions.

The HIS/RIS 7 generates the imaging order information in accordance with a registration operation conducted by an operator based on a medical interview result. The imaging order information contains patient information such as a name, sex, age, height, and weight of the subject patient, and information related to imaging reservation such as an imaging region, an imaging orientation, a body position (standing or decubitus position), an imaging method. The imaging order information is not limited to those listed above as examples, and may include other information or may be a part of the information listed above.

The diagnostic console 8 is a computer device which obtains a medical image from the server device 10 and displays the obtained image for a medical doctor to interpret for diagnosis.

The FPD 9 is a radiation detector which is configured by a controlling part, a detecting part, a storage part, a connector, a battery, a wireless communication part, and so on.

The detecting part of the FPD 9 has, for example, a glass substrate, and a plurality of detecting elements which are two-dimensionally arrayed at a given position on the substrate. The detecting elements detect radiation which has been emitted from the radiation source 3 and transmitted at least through the subject in accordance with the intensity thereof, convert the detected radiation into electric signals, and accumulate the electric signals therein. The detecting elements are made from semiconductor image sensors such as photodiodes. Each of the detecting elements is connected to a switching part such as a TFT (thin film transistor), and the switching part controls accumulation and reading of electric signals.

The controlling part of the FPD 9 controls the switching part of the detecting part based on the image readout conditions inputted from the imaging console to switch reading of electric signals accumulated in each of the detecting elements. Then, the controlling part of the FPD 9 generates image data (a still image) by reading the electric signals accumulated in the detecting part. Thereafter, the controlling part outputs the generated image data to the imaging console 5 through the connector and the bucky device 1 or 2. Note that each pixel which constructs the generated still image represents a signal value (referred to as a concentration value) which has been outputted from each of the detecting elements of the detecting part.

The connector of the FPD 9 is connected to a connector on the side of the bucky device 1 or 2, and transmits/receives data to/from the bucky device 1 or 2. Further, power which has been supplied from the connector of the bucky device 1 or 2 is distributed by the connector of the FPD 9 to each functional part. Alternatively, a buttery-charging construction may also be applied.

Further, the FPD 9 is constructed to be driven by a battery and communicate wirelessly when it is used as a lone FPD, and can be switched from the battery-driven/wireless communication system to a wired/power supply system by connecting the connectors to one another when the FPD 9 is mounted on the bucky device 1 or 2. Therefore, still images of a plurality of patients can be captured continuously without worrying about the battery running down.

The server device 10 is provided with a database which stores image data of medical images and radiogram interpretation reports transmitted from the imaging console 5 in correspondence with the imaging order information. Moreover, the server device 10 reads a medical image from the database according to a request from the diagnostic console 8, and transmits the medical image to the diagnostic console 8.

(Imaging Operations)

Next, imaging operations in the medical imaging system 100 will be explained.

Figure 3:
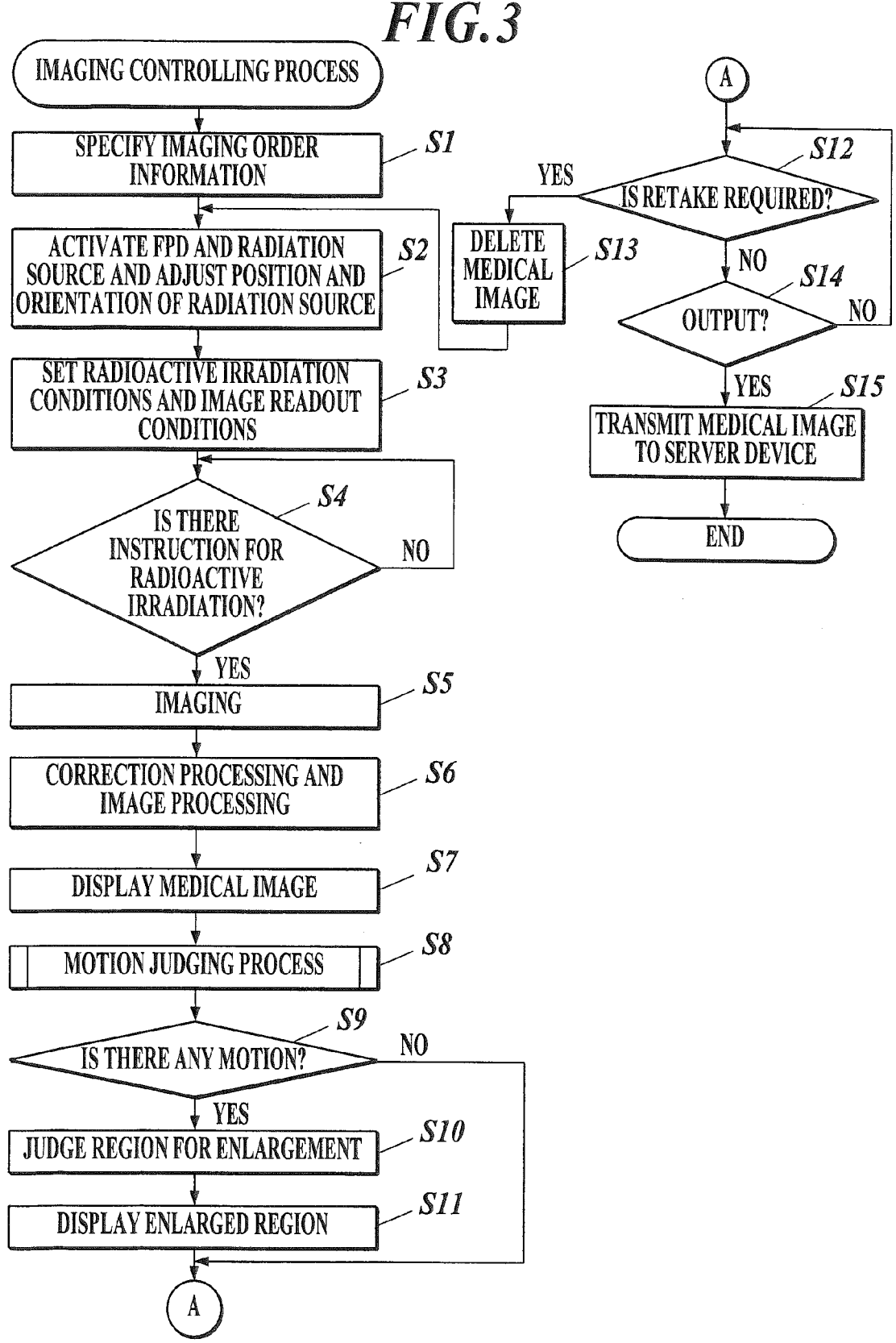
FIG. 3 is a flowchart showing imaging controlling process which is executed by a controlling section of the imaging console.

FIG. 3 shows a flow of the imaging controlling process which is executed in the imaging console 5. The imaging controlling process shown in FIG. 3 is executed in collaboration of the controlling section 51 of the imaging console 5 and programs stored in the storage section 52.

First, an operator such as a radiographer sets the FPD 9 onto the bucky device 1 or 2. Then, the operator operates the inputting section 53 of the imaging console 5 so that an imaging order list screen showing a list of imaging order information is displayed on the display part 54. Thereafter, by operating the inputting section 53, the operator specifies imaging order information of an imaging subject and an ID of the bucky device to be used for imaging from the imaging order list screen.

In the imaging console 5, once imaging order information of an imaging subject and the bucky ID are specified by the inputting section 53 (step S1), the radiation source 3 and the FPD 9 are activated, and the orientation and position of the radiation source 3 are adjusted in accordance with the bucky device to be used. After the positions and the like of the FPD 9 and the bucky device are adjusted by a radiographer in accordance with a subject, the orientation and position of the radiation source 3 are adjusted accordingly (step S2). Further, radioactive irradiation conditions and imaging readout conditions corresponding to an imaging region are read out from the storage section 52, radioactive irradiation conditions are set in the radiation source 3, and image readout conditions are also set in the FPD 9 through the bucky device (step S3). When the preparations for imaging are completed, the radiographer operates the operating station 6 and inputs a radioactive irradiation instruction.

Once the radioactive irradiation instruction is inputted from the operating station 6 (step S4: YES), the radiation source 3 and the FPD 9 to be used for imaging are controlled to conduct imaging of the subject (step S5). Specifically, a medical image which is a still image of a subject, and one or more dark images for offset correction are captured under the conditions set in step S3. Image data of the medical image and the dark image generated by the imaging is inputted to the imaging console 5 through the bucky device from the FPD 9 and stored in the storage section 52.

Next, correction processing and image processing are executed on the medical image which was obtained from the imaging (step S6), and the process moves on to step S7. In step S6, correction processing such as offset correction processing, gain correction processing, defective pixel correction processing, and lag correction processing is executed as necessary using the aforementioned dark image based on the characteristic information of the FPD 9 stored in the storage section 52. Also, gradation processing, frequency enhancement processing, and graininess suppression processing are executed as image processing depending on the imaged region.

When there is more than one FPDs 9, the characteristic information thereof may be stored in the storage section 52 in correspondence with the respective IDs of the FPDs 9, the ID may be obtained from the FPD 9 through the bucky device to be used, and the correction processing and the image processing may be executed based on the characteristic information which correspond to the obtained ID.

A medical image which has undergone the correction processing and image processing is stored in the storage section 52.

Next, an image confirmation screen which displays the medical image after the correction processing and image processing is displayed on the display part 54 (step S7), and a motion judging process is executed (step S8) at the same time. The image confirmation screen displays a medical image after the correction processing and the image processing is executed thereon. Although not illustrated specifically, the image confirmation screen is a screen which does not show an enlarged image display box 541a and a popup screen 541b in a motion warning screen 541 illustrated in FIG. 14. The rest of the screen layouts and buttons displayed are the same as those of the motion warning screen 541.

Herein below, an example of the motion judging process which is executed at step S8 in FIG. 4 will be explained in detail. As one embodiment, a process will be explained which judges whether there is any motion in a subject during image capture in a medical image of the front chest.

Figure 4:
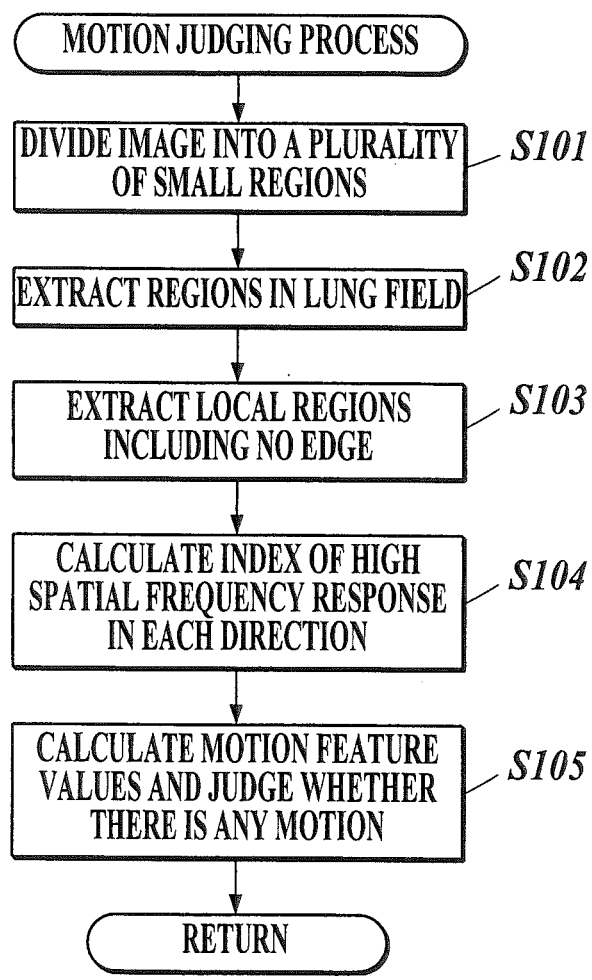
FIG. 4 is a flowchart showing a motion judging process which is executed at step S8 in FIG. 3.

FIG. 4 shows a flow of the motion judging process which is executed in the imaging console 5 at step S8. The motion judging process shown in FIG. 4 is executed in collaboration of the controlling section 51 of the imaging console 5 and the programs stored in the storage section 52.

First of all, the algorithms for the motion judging process shown in FIG. 4 will be outlined with reference to FIGS. 5A to 5C and FIG. 6.

Figure 5A:
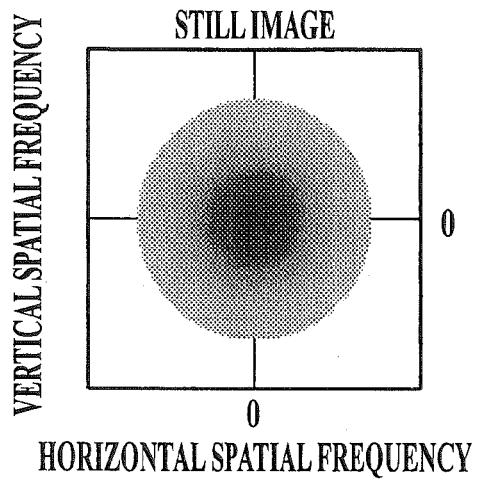
FIG. 5A is a view schematically showing a spatial frequency response in a still image.
Figure 5B:
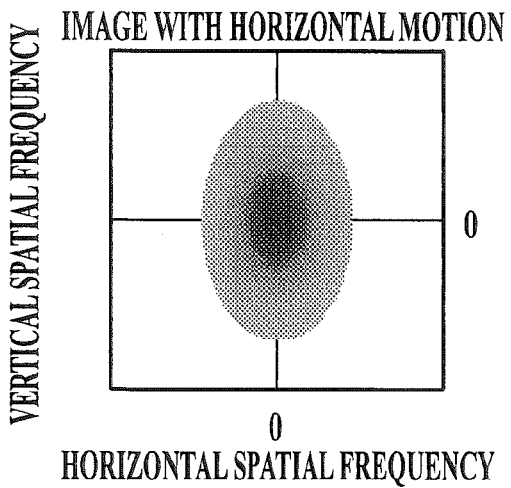
FIG. 5B is a view schematically showing a spatial frequency response in a still image containing lateral motions (a motion image)
Figure 5C:
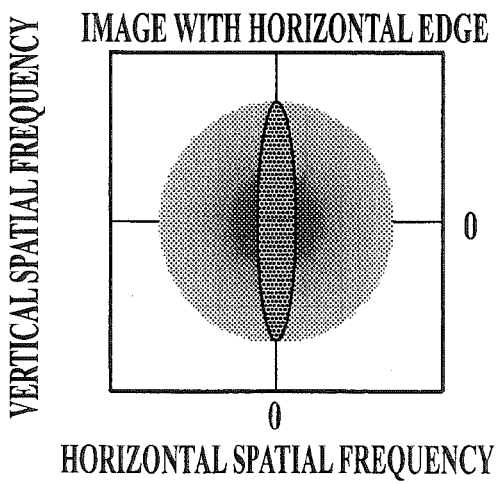
FIG. 5C is a view schematically showing a spatial frequency response in an image which contains a lateral edge.

FIGS. 5A to 5C are views which schematically show spatial frequency responses in medical images.

In each of FIGS. 5A to 5C, the horizontal axis represents a spatial frequency range in the horizontal direction, and the vertical axis represents a spatial frequency range in the vertical direction. Both axes show that the center is the lowest frequency range and the frequency range is highest at a point farthest from the origin (center). In FIGS. 5A to 5C, the strength of the spatial frequency response in each range is expressed as color density, and the density is higher for stronger response.

FIG. 5A is a view schematically showing spatial frequency response in a still image. As illustrated in FIG. 5A, the high spatial frequency response in a still image is the same level in average in every direction.

FIG. 5B is a view schematically showing spatial frequency response in a still image containing lateral motions (motion image). In a motion image, the spatial frequency response is reduced in the direction of the motion, and the strength of the response varies depending on the direction. When there are motions in the lateral direction, the spatial frequency response in the lateral direction becomes weaker as illustrated in FIG. 5B.

Figure 6:
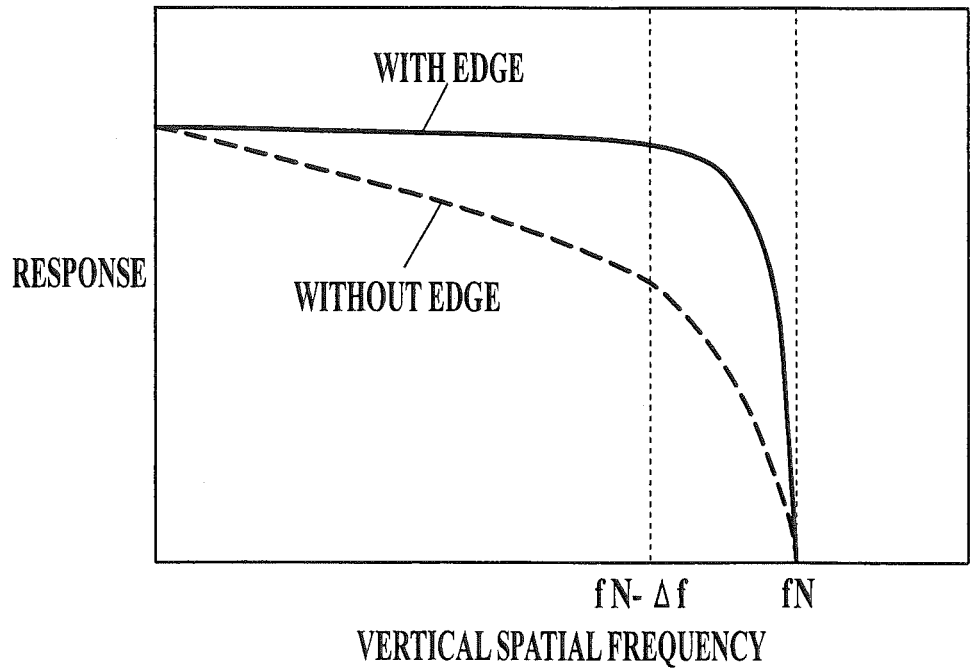
FIG. 6 shows a relation between a vertical spatial frequency and a response in an image which contains a lateral edge and an image which contains no edge.

FIG. 5C is a view schematically showing spatial frequency response in an image which contains an edge in the lateral direction. Further, FIG. 6 is a view which shows a relationship between the vertical spatial frequency and response in an image containing an edge in the lateral direction and in an image containing no edge. As illustrated in FIG. 5C, in the image containing an edge, strong high spatial frequency is generated in a direction perpendicular to the edge, and the strength of the response varies depending on a direction. Also, as shown in FIG. 6, in the image containing an edge, the response in the high spatial frequency range is stronger than the image containing no edge.

With the algorithms for the motion judging process shown in FIG. 4, existence of motions is judged based on the characteristics of the spatial frequency responses in these still images, the motion image, and in the edge image.

In the motion judging process, a medical image which is subjected to the motion judging process (a medical image after the correction processing and the image processing executed at step S6) is first divided into a plurality of small regions (for example, rectangular regions of 2 mm×2 mm) (step S101). By dividing the medical image subjected to the processing into small regions, the region of the lung field which is a subject region contained in the medical image is also divided into small regions.

Next, the region in the lung field is extracted (step S102).

Figure 7:
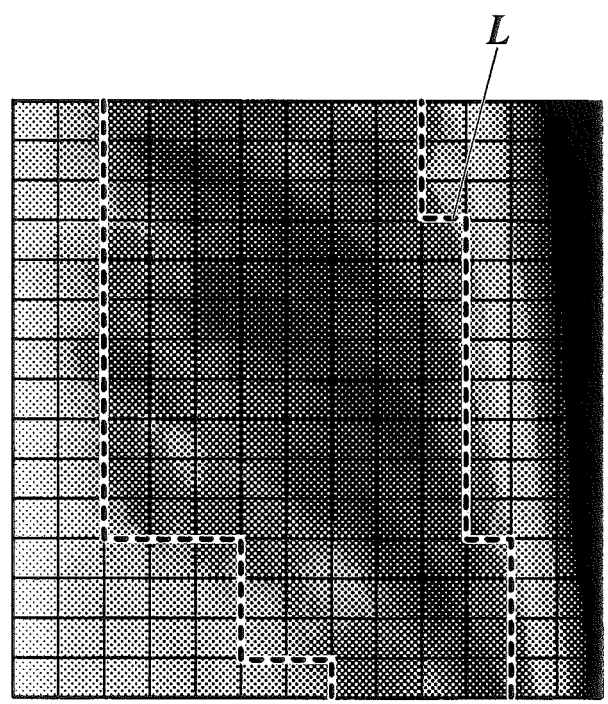
FIG. 7 is a view showing an example of a lung field which is extracted from a medical image.
Figure 8:
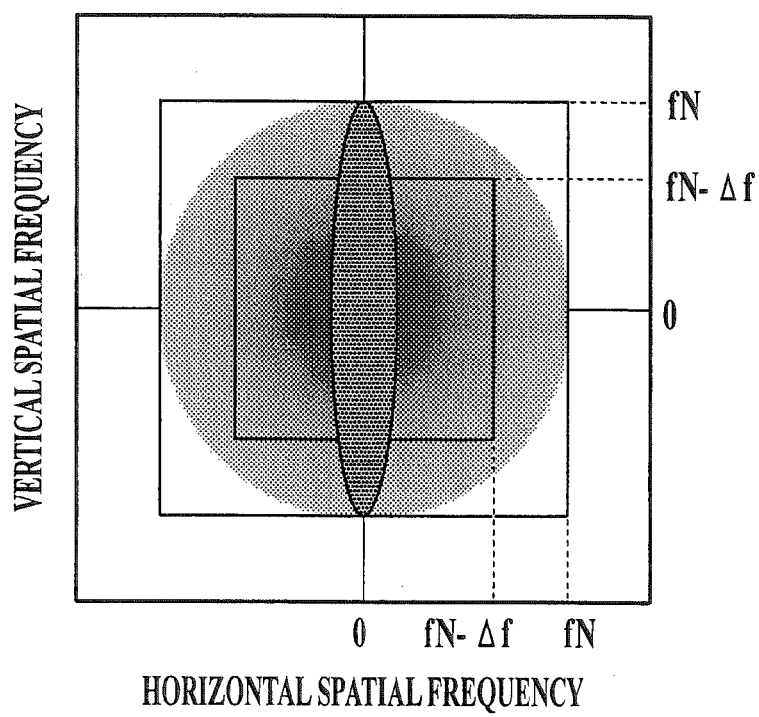
FIG. 8 is a view for explaining a range in which a maximum value or an integral value of response is calculated.

Roughly three peaks appear in a signal value histogram of the still image of the chest area. A peak that appears in a high intensity area is a direct X-ray region in which X-ray did no go through a subject and direct X-ray is detected. A peak which appears in a low intensity area is the trunk region such as the heart and bones where X-ray is less transmissive. A peak that appears between the above two peaks is a lung field region through which the X-ray has gone through. Thus, at step S102, a threshold value for the trunk region and the lung filed region (a threshold value 1 on the low intensity side), and a threshold value of the direct X-ray region (a threshold value 2 on the high intensity side) are obtained from the signal value histogram of the medical image to be processed, respectively, by discriminatory analysis or the like. Then, a region containing a signal value between the threshold value 1 and the threshold value 2 is extracted as a lung field region. FIG. 7 shows an example of a lung field region extracted at step S102. The region L enclosed by a heavy dotted line is the lung region.

It should be noted that a lung field region may be extracted before the region in the lung field is divided into small regions.

Next, local regions which do not include any edge are extracted from the extracted lung region (step S103).

Figure 9:
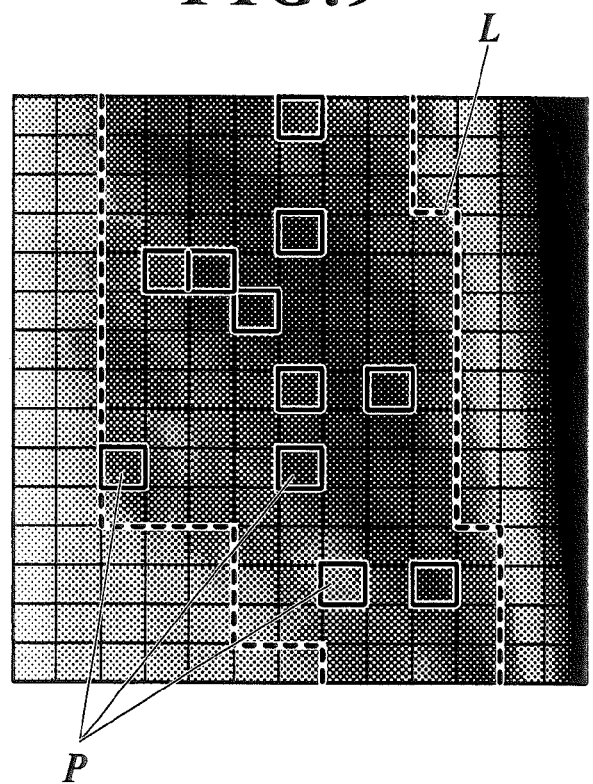
FIG. 9 is a view showing an example of local regions which do not contain the edge that is extracted at step 5103 in FIG. 4.

In a region which includes an edge such as a rib bone, a number of high spatial frequency components are contained as stated earlier. Therefore, at step S103, high spatial frequency components are extracted by passing the high-pass filter which only extracts predetermined range of high spatial frequency components. Thereafter, a maximum value or an integral value of the responses in the range between the Nyquist frequency fN of the extracted high spatial frequency components and fN−Δf (Δf represents a predetermined value) are calculated. Then, either the calculated maximum value or the integral value is compared to a predetermined threshold value which is set for each of the maximum value the integral value. When the maximum value or the integral value is greater than the threshold value thereof, it is judged that the small region contains an edge. Since a region containing no edge is extracted here, the calculated maximum value or the integral value is compared to the threshold value which is previously set for each of the values, and a small region having the threshold value or smaller is extracted as a region containing no edge. FIG. 9 shows local regions extracted at step S103 where no edge is included. Small regions P in the drawing are the extracted local regions. FIG. 9 only shows some of the small regions P but the small regions enclosed by rectangular shapes with the same type of line and the same size are also small regions P. The edge detection may be performed by using a different method (for example, a method using a vertical profile and a horizontal profile for a medical image).

Next, an index value which expresses high spatial frequency response in each direction is calculated in each of the extracted local regions (step S104).

Figure 10:
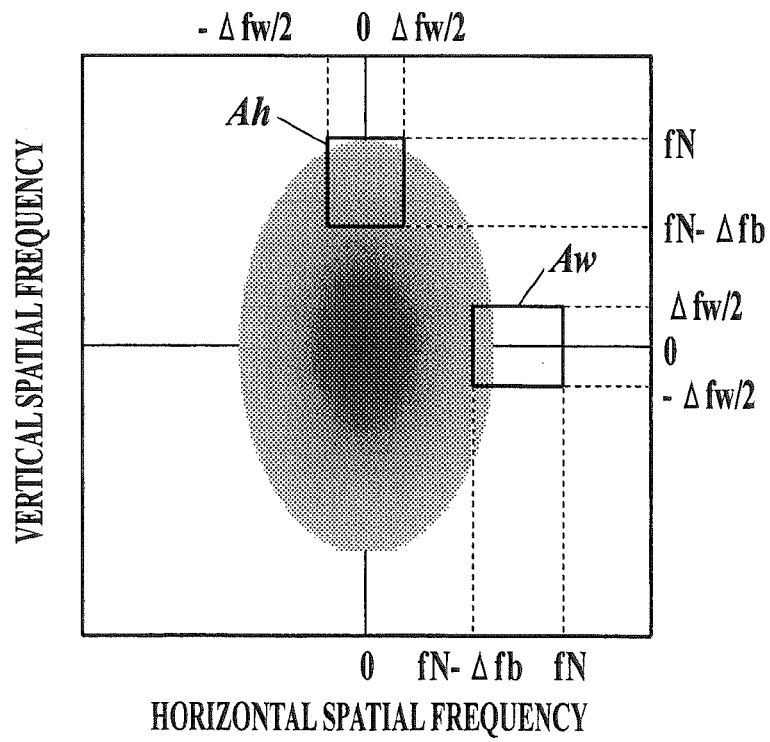
FIG. 10 is a view for explaining ranges which are objects of calculation of indexes of high spatial frequency responses in the vertical and lateral directions.

With regard to the high spatial frequency components to the vertical direction, response is obtained in each range (a range contained in Ah illustrated in FIG. 10) surrounded by a range between −Δfw/2 and Δfw/2 in the spatial frequencies in the horizontal direction (Δfw is a predetermined value), and a range between the Nyquist frequency fN and fN−Δfb (Δfb is a predetermined value) in the spatial frequencies in the vertical direction, as shown in FIG. 10. A maximum value or an integral value of the obtained response is calculated as an index Rh of response of high spatial frequency components in the vertical direction.

With regard to the high spatial frequency components to the horizontal direction, response is obtained in each range (a range contained in Aw illustrated in FIG. 10) surrounded by a range between −Δfw/2 and Δfw/2 in the spatial frequencies in the vertical direction, and a range between the Nyquist frequency fN and fN−Δfb in the spatial frequencies in the horizontal direction, as shown in FIG. 10. A maximum value or an integral value of the obtained response is calculated as an index Rw of response of high spatial frequency components in the horizontal direction.

Figure 11:
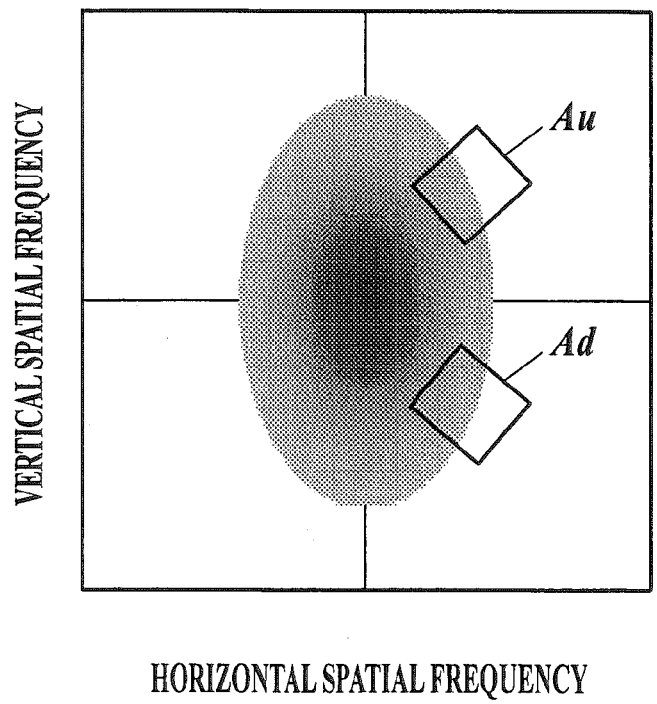
FIG. 11 is a view for explaining ranges which are objects of calculation of indexes of high spatial frequency responses in oblique directions.

Hereinafter, an integral value will be used. Also, the description is given regarding a range in the vertical and horizontal directions only, but the index values of responses may be calculated in ranges in four directions, where two oblique directions Au and Ad shown in FIG. 11 are added.

Next, based on the response index values calculated for the respective local regions, motion feature values are calculated. Based on the calculated motion feature values, it is judged whether there is any motion in a subject during image capture (step S105).

Figure 12:
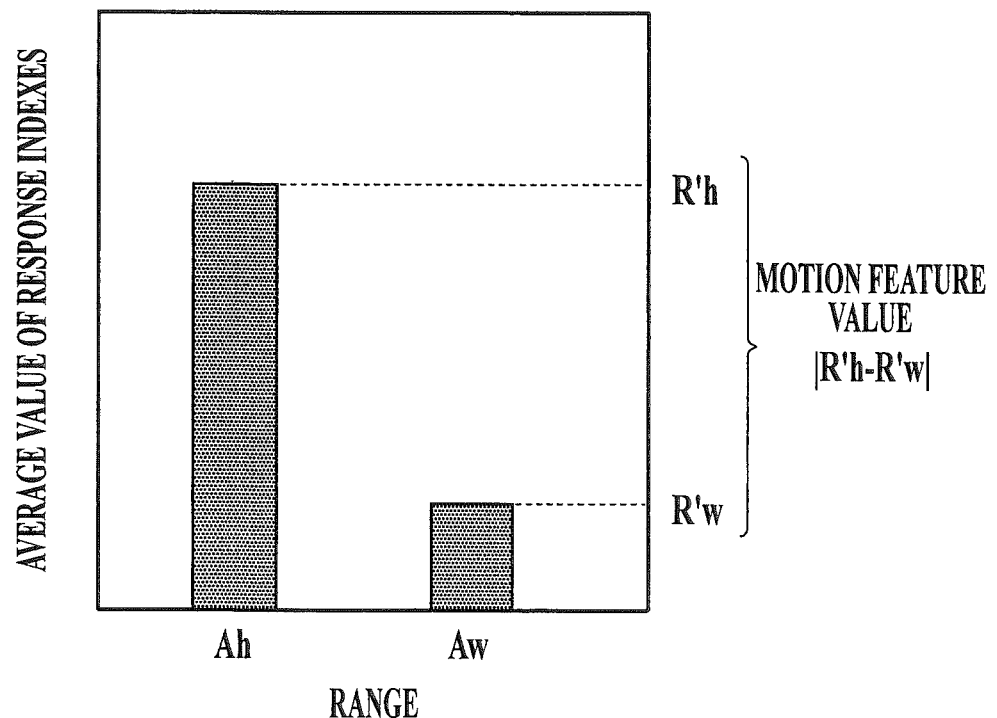
FIG. 12 is a view for explaining how to calculate motion feature values.

In step S105, as shown in FIG. 12, average values Rh' and Rw' are calculated for respective directions with regard to the responses Rh and Rw for the respective directions calculated in each of the local regions. Then, an absolute value of a difference between the calculated Rh' and Rw', that is |R'h−R'w|, is calculated as a motion feature value. When the motion feature value is greater than a predetermined threshold value, it is judged that there is a motion in a direction of the smaller value (the horizontal direction in FIG. 12). When there are four directions where two oblique directions are added, an average value for each direction is calculated with regard to the response index in each direction calculated for each local region. Thereafter, an absolute value of a difference between the average values in the vertical and horizontal directions and an absolute value of a difference between the oblique directions are calculated and compared to each other, and the one that is greater is used as the motion feature value. Once the judgment of existence of motion is ended, the process moves on to step S9.

In step S9 in FIG. 3, it is judged whether there is any motion in the subject based on the judgment result of the motion judging process. When it is judged that there is no motion in the subject (step S9; NO), the process moves on to step S12.

On the other hand, when it is determined that there is a motion in the subject (step S9; YES), a region for enlargement is decided in order to display an enlarged part of a motion, based on positional information and high spatial frequency components of the local regions without edges, which were extracted in the motion judging process (step S10).

Figure 13A:
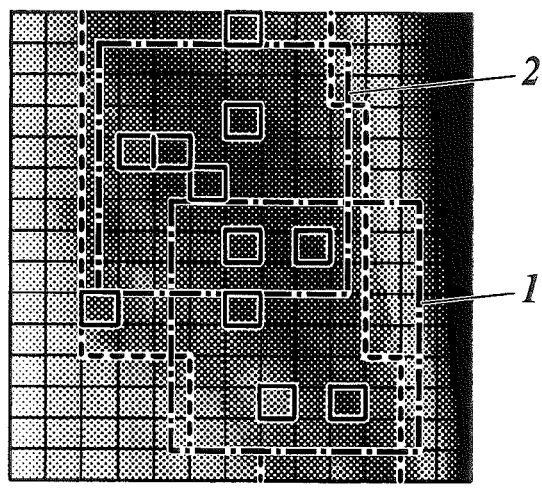
FIG. 13A is a view showing a process for determining an enlargement region for an enlarged display on a motion warning screen (a first step)
Figure 13B:
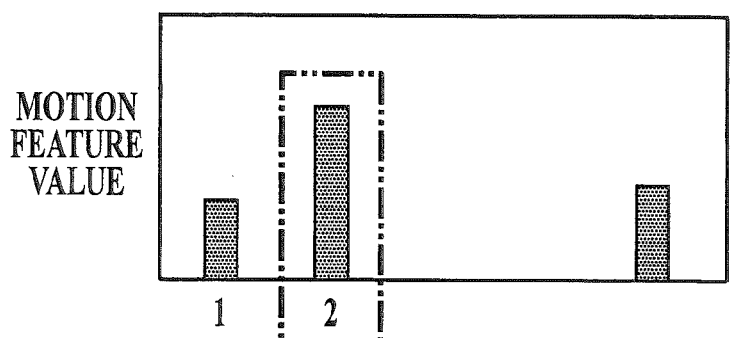
FIG. 13B is a view showing the process for determining an enlargement region for the enlarged display on the motion warning screen (a second step)
Figure 13C:
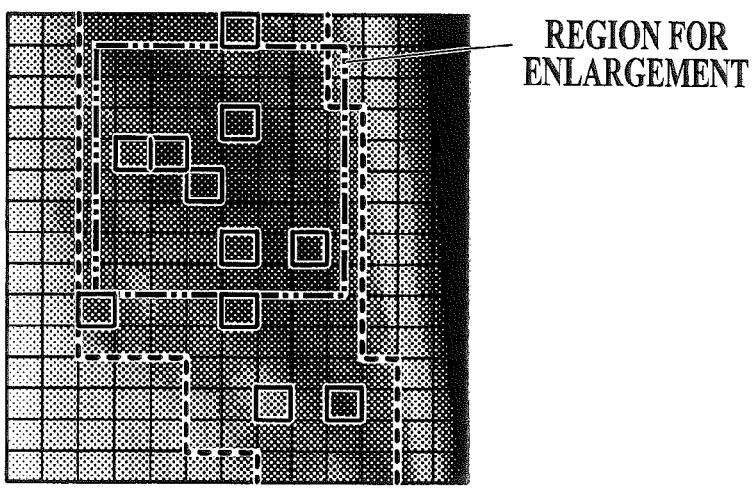
FIG. 13C is a view showing the process for determining an enlarged region for the enlarged display on the motion warning screen (a third step)

FIGS. 13A to 13C show a decision process of an enlargement region at step S10 of FIG. 3. As shown in FIG. 13A, a plurality of candidate regions for enlargement (a region 1 and a region 2 in FIG. 13A) having a given size are set in the lung field region. Then, as shown in FIG. 13B, total sums of the motion feature values calculated from the local regions in the respective candidate regions for enlargement are obtained. Thereafter, as illustrated in FIG. 13C, a candidate region for enlargement having the largest total sum of the motion feature values (the region 2 in FIGS. 13A and 13B) is decided as the enlargement region.

Next, the display section 54 displays the motion warning screen 541 in which the decided enlargement region is displayed (step S11).

Figure 14:
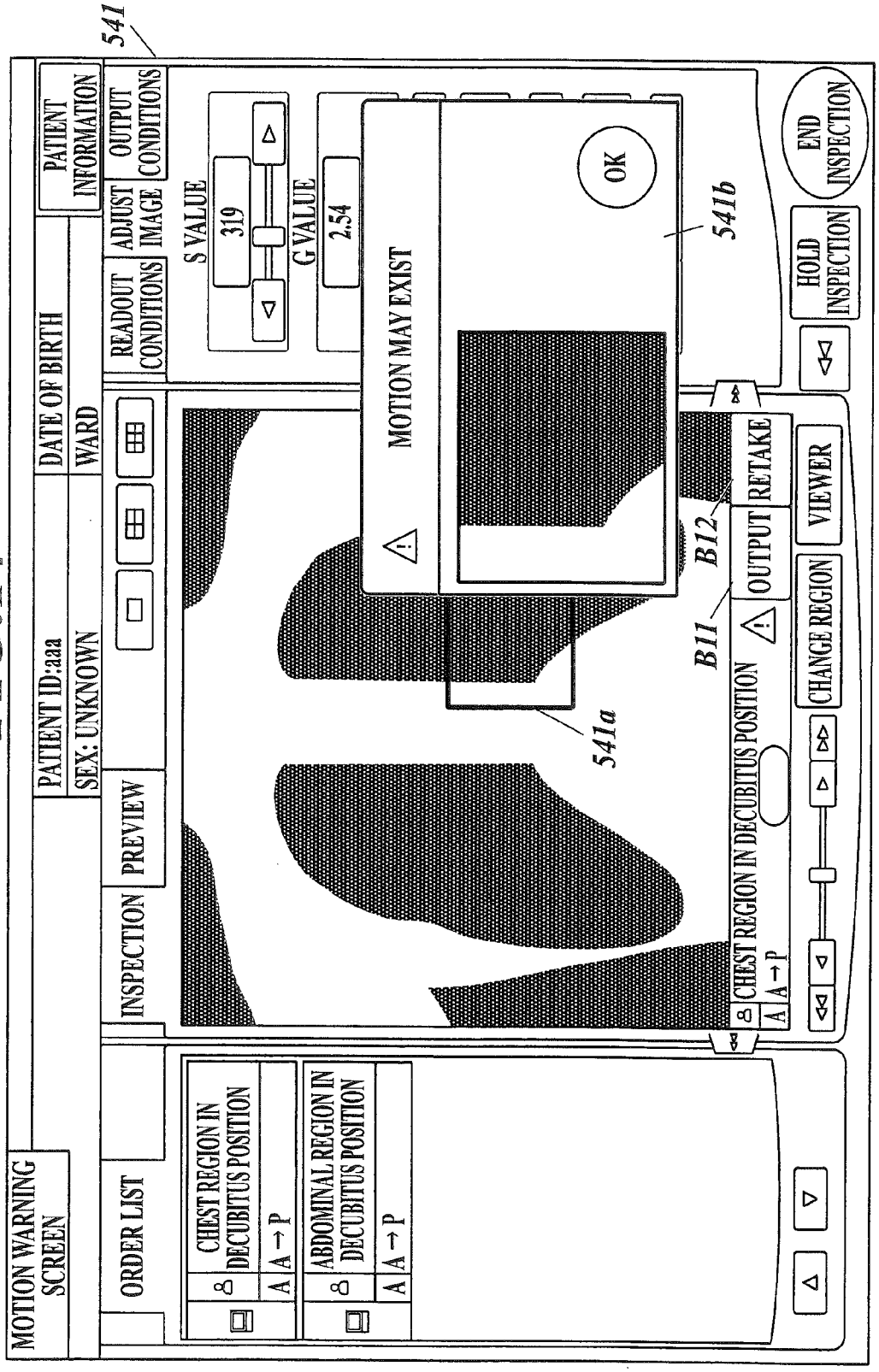
FIG. 14 is a view showing an example of the motion warning screen which is displayed at step S11 shown in FIG. 3.

FIG. 14 shows an example of the motion warning screen 541. In the motion warning screen 541, a box 541a which indicates the enlargement region decided as above is displayed in an overlapping fashion on the medical image (after image processing) obtained by image capture. At the same time, the screen 541b pops up which displays an enlarged image of the above-mentioned enlargement region and a warning message such as "motion may exist". In addition, an output button B11 and a retake button B12 are displayed on the motion warning screen 541. The output button B11 is a button to give an instruction to output and save the displayed medical image in the server device 10. The retake button B12 is a button to give an instruction to discard the displayed medical image and have a retake.

In step S12, when the retake button B12 is depressed from the inputting section 53 (step S12; YES), the medical image after the image processing stored in the storage section 52 is deleted (step S13), and the process returns to step S2. On the contrary, when the retake button is not depressed from the inputting section 53 (step S12; NO), and the output button B11 is depressed (step S14; YES), the image data of the medical image that has gone through image processing is transmitted by the network communication section 56 to the server device 10 in correspondence with the imaging order information which was specified at step S1 (step S15), and the imaging controlling process ends. In the server device 10, the received image data of the medical image is saved in the database in correspondence with the imaging order information.

As described above, according to the medical imaging system 100, the controlling section 51 of the imaging console 5 extracts a subject region from a medical image which is a still image captured by imaging of a subject, and extracts local regions which do not contain high spatial frequency components caused by an edge, from the subject region. Then, the controlling section 51 extracts high spatial frequency components from the extracted local regions, judges whether there is a motion in the subject during image capture based on the extracted high spatial frequency components, and causes the output unit to output the judgment result.

Thus, since it is judged whether there is a motion in the subject by using regions which are not affected by an edge portion of a structural object, it becomes possible to judge existence of a motion accurately.

Further, high spatial frequency components are extracted from each of the plurality of local regions, and existence of motion in a subject during image capture is judged based on the high spatial frequency components extracted from the plurality of local regions. Therefore, noises and local regions themselves are less influential than the case where high spatial frequency components extracted from a single local region is used, and judgment of existence of a motion can be made even more accurately.

Also, high spatial frequency components are extracted in a plurality of directions, and it is judged whether there is a motion in a subject during image capture based on the extracted high spatial frequency components in the plurality of directions. Therefore, the direction of the motion can be specified, and judgment of existence of motion can be made even more accurately.

Yet further, when it is judged that there is a motion, the controlling section 51 decides a region for enlarged display from a medical image based on the positional information of the extracted local regions and the high spatial frequency components extracted from local regions, and displays an enlarged image of the decided region on the display section 54. Therefore, an operator is able to confirm a motion on the image easily.

The above-mentioned first embodiment is one of preferred examples, and the present invention is not limited thereto.

The first embodiment described above was explained that a medical image obtained from the FPD 9 is displayed on the display section 54 for the purpose of confirmation and is used for the motion judging process. However, for example, thinning process may be executed by the FPD 9 on a medical image, and the thinned medical image may be displayed on the display section 54 for the purpose of confirmation and used for executing the motion judging process. This way, time required for data transfer from the FPD 9, image processing, and motion judgment can be reduced.

Further, in the foregoing first embodiment, the motion judging process was explained using the exemplary case where the imaging region is the front chest. However, for other imaging regions, the same method as the aforementioned motion judging process can be employed except that the area of interest extracted at step S102 differs depending on the imaging region.

Moreover, in the foregoing first embodiment, it was explained that the display section 54 serves as an outputting unit which performs display output of a warning (judgment result) when it is judged that there is a motion in a subject. However, the warning may be outputted from an audio output device, for example. Also, the foregoing embodiment was described using an exemplary case where the warning that indicates a judgment result is outputted when it is judged that there is a motion in a subject. However, even when it is judged that there is no motion in a subject, the judgment result may be displayed on the display section 54.

Yet further, although the medical imaging system which generates a medical image using a FPD was explained as an example in the first embodiment, a unit for generating a medical image is not limited thereto, and, for example, CR may be used instead.

Furthermore, the above description disclosed an exemplary case where a HDD, a semiconductor non-volatile memory or the like is used as a computer-readable medium for the programs according to the present invention. However, the computer-readable medium is not limited thereto. As other computer-readable medium, a portable storage medium such as a CD-ROM maybe applied. Also, carrier wave is applicable as a medium which provides data of the programs according to the present invention through a communication line.

[Second Embodiment]

A second embodiment of the medical imaging system will be explained below.

In radiography, a retake is required if a medical image obtained from imaging does not meet criteria for a diagnostic medical image (a defective image inappropriate for diagnosis), such as an image in which a subject is inappropriately positioned and a specific region is thus missing, an image including a motion in a subject, and an image picked up by an insufficient dose of radiation. Also, it is preferred that judgment of necessity of a retake can be made at an early stage.

There is a conventionally-known radiological image generating system in which a reduced image of a medical image captured by a FPD (flat panel detector) is transferred to a console prior to the medical image, and the reduced image is displayed at an early stage on the console as a preview image. Thus, it is possible to confirm promptly whether the medical image captured is a defective image which has positioning error or includes a motion and thus requires a retake.

Also, such system has been proposed that provides a warning when an image is inappropriate for diagnosis by analyzing the medical image obtained from radiological imaging.

In the radiological image generating system which displays a preview image, the preview image can be confirmed immediately after the image capture. Therefore, if the medical image is defective and improper for diagnosis, the image can be confirmed without releasing a patient from positioning and a retake can be done only after making minor adjustments of the positioning. However, for a seriously ill patient, just holding a positioning itself during image capture is a painful experience, so it is desired to judge whether a medical image is properly captured as soon as possible after image capture and release a patient from the positioning.

Also, since it is difficult for a critically-ill patient to move to a radiography room, image capture is conducted at the bedside using a visiting car. In this case, a medical image is confirmed on a portable console. However, since a screen size of such a console is small for portable convenience, it is more difficult to confirm an image than a stationary console. Moreover, since a preview image is inferior to a diagnostic medical image in resolution and image quality, an image which requires a retake due to a positioning error or a motion may have been overlooked. In addition, when an operator tries to confirm a preview image more carefully in order to reduce the risk of overlooking inappropriate images, more time is needed for the confirmation, causing a large burden on a patient to keep the positioning.

Meanwhile, in the case of the system which provides a warning when image is not appropriate for diagnosis by analyzing a diagnostic medical image, it takes time until the medical image for diagnosis is obtained and displayed on the console. Therefore, it was required to release a patient from positioning once to confirm the medical image after image capture in order to reduce the positioning burden on the patient. When defectiveness of the medical image is noticed because of the warning which is provided after the medical image is obtained by the console, re-positioning is required, and it has been a problem that heavy burdens are thus caused on both a radiographer and a patient.

Therefore, in the second embodiment, a medical imaging system will be explained in which a radiographer is enabled to instantaneously identify a defective image which does not satisfy predetermined criteria for a diagnostic medical image, thus preventing a defective image from being overlooked and reducing a burden on a patient.

(Configuration of Medical Imaging System)

First of all, the configuration of the medical imaging system according to the second embodiment will be explained. An example of the whole configuration of the medical imaging system according to the second embodiment is similar to that of the medical imaging system 100 which was described in the first embodiment with reference to FIG. 1. Having said that, there are some minor differences in individual constituents, and such differences will be explained below.

A radiation source 3 is, for example, hung from the ceiling of a radiography room Rm, is activated based on an instruction from an operating station 6 for image capture, and is adjusted to given position and orientation by a non-illustrated driving mechanism. Then, by changing a direction of radioactive irradiation, the radiation source 3 is able to emit radiation (X-ray) to a FPD 9 which is mounted onto a bucky device for radiography in a standing position 1 or a bucky device for radiography in a decubitus position 2. Also, the radiation source 3 emits radiation once in accordance with an instruction from the operating station 6 to capture a still image.

An imaging console 5 is a medical image processing device which is designed for executing correction processing and image processing on a reduced image (preview image) of a medical image transmitted from the FPD 9 and displaying the reduced image, as well as executing correction processing and image processing on a medical image transmitted from the FPD 9 to generate and display a medical image used for diagnosis. The imaging console 5 is connected to a HIS/RIS (hospital information system/radiology information system) 7, a diagnostic console 8, a server device 10, and so on via a LAN (local area network), displays a list of imaging order information transmitted from the HIS/RIS 7 and sends the imaging order information and a corresponding medical image to the server device 10.

Figure 15:
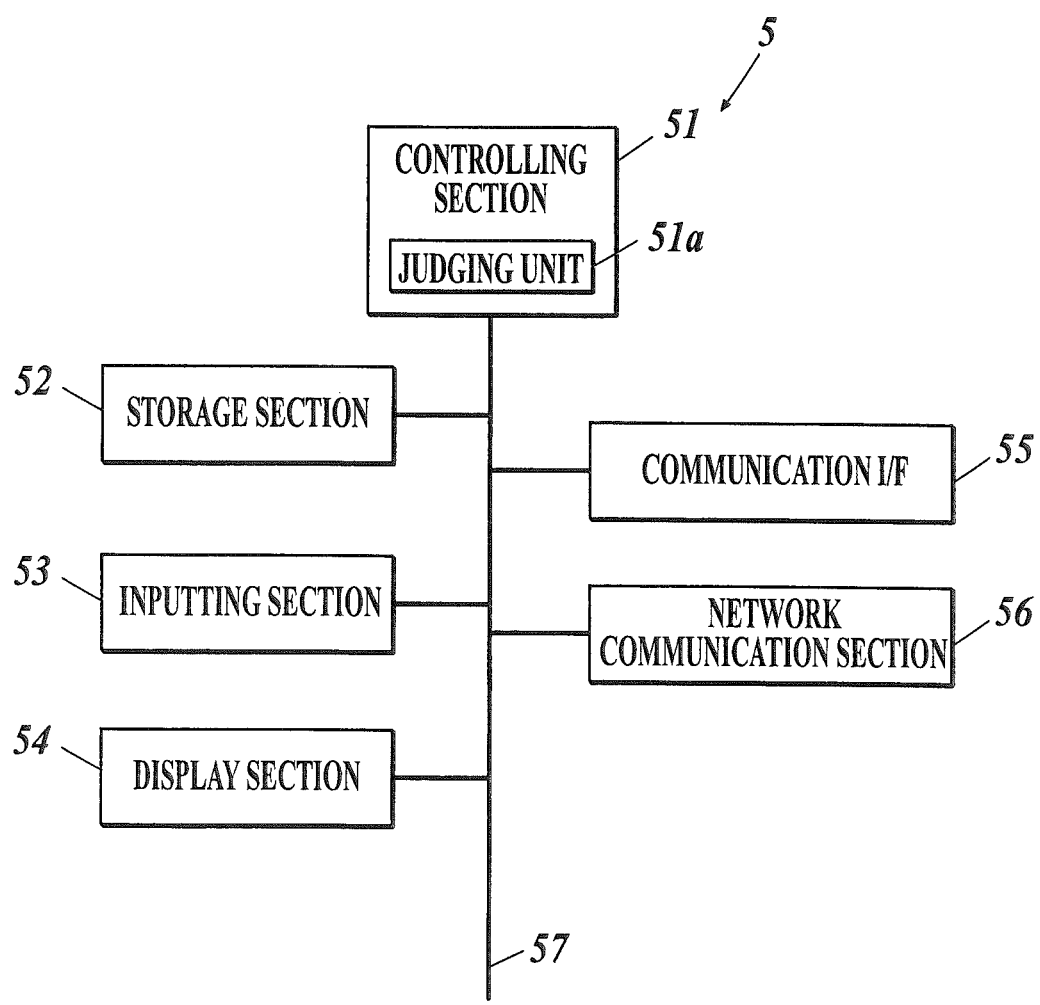
FIG. 15 is a block diagram showing a functional configuration of an imaging console according to a second embodiment.

FIG. 15 shows a configuration example of a main part of the imaging console 5 according to the second embodiment. As illustrated in FIG. 15, in the second embodiment, a controlling section 51 of the imaging console 5 includes a judging unit 51a (described later in detail). Also, the controlling section 51 achieves functions as a region extracting unit, a motion judging unit and a controlling unit by executing the process on the imaging consol side in a medical image generating process shown in FIG. 16.

The rest of the sections constructing the imaging console 5 are similar to those explained in the first embodiment, so the same explanation is applied thereto.

The operating station 6 is an input device which is connected to the radiation source 3 in the radiography room, and is for inputting radioactive irradiation instructions for the radiation source 3, settings of radioactive irradiation conditions and so on. In this embodiment, the operating station 6 includes a storage device in which imaging conditions (radioactive irradiation conditions and image readout conditions) are stored in correspondence with imaging regions, and sets the radioactive irradiation conditions in the radiation source 3 in accordance with a selected imaging region. The radioactive irradiation conditions include, for example, a value of X-ray tube, current, a value of X-ray tube voltage, a kind of filter, and a SID (source to image-receptor distance).

The controlling part of the FPD 9 controls the switching part of the detecting part based on the image readout conditions stored in the storage section to switch reading of electric signals accumulated in each detecting element. Then, the controlling part of the FPD 9 generates image data of a medical image (a still image) by reading the electric signals accumulated in the detecting part. Thereafter, the controlling part of the FPD 9 generates a preview image after executing a reduction process on a generated medical image, and outputs the preview image and image data of the medical image to the imaging console 5 through the connector and the bucky device 1 or 2. This means that the FPD 9 functions as a medical image generating unit and a preview image generating unit. Note that each pixel which constructs the generated still image represents a signal value (referred tows a concentration value herein) which has been outputted from each of the detecting elements of the detecting part.

The rest of the configuration of the medical imaging system 100 is similar to those explained in the first embodiment, and the same description thereof will be applied thereto.

(Imaging Operations)

Next, the imaging operations in the medical imaging system 100 according to the second embodiment will be explained.

Figure 16:
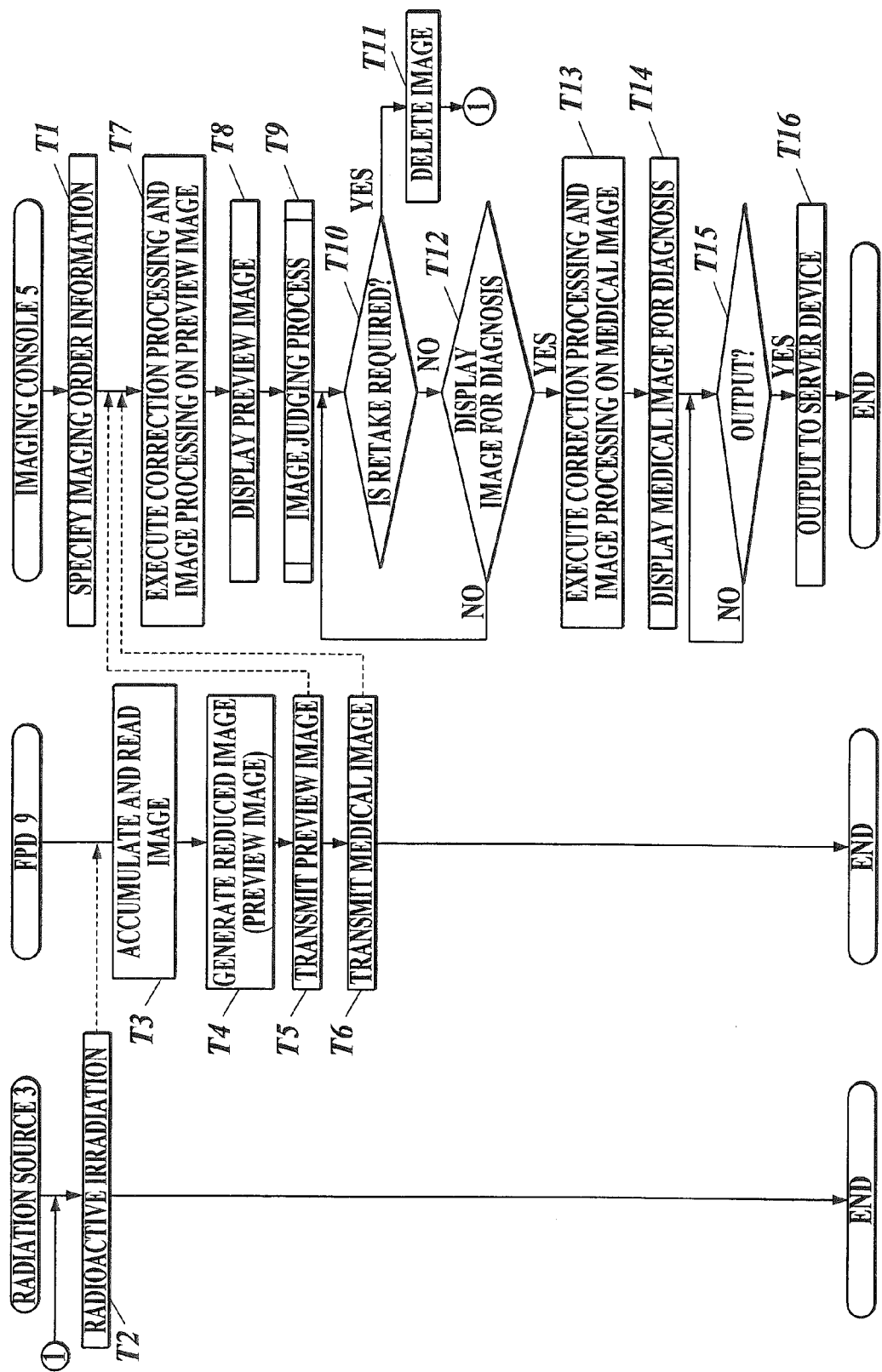
FIG. 16 is a flowchart showing a medical image generating process which is executed by a controlling section of the imaging console according to the second embodiment.

FIG. 16 shows a flow of the medical image generating process which is executed in the medical imaging system 100.

First, an operator such as a radiographer operates an inputting section 53 of the imaging console 5 so that an imaging order list screen showing a list of imaging order information is displayed on the display section 54. Thereafter, by operating the inputting section 53, the operator specifies imaging order information of an imaging subject from the imaging order list screen (steps T1).

Next, the operator mounts the FPD 9 on the bucky device 1 or 2, and sets the position of the subject by adjusting the orientations of the bucky device and the radiation source 3. Also, the operator sets radioactive irradiation conditions based on an imaging region from the operating station 6, and instructs radioactive irradiation. Once the instruction of radioactive irradiation from the operating station 6 is received, the radiation source 3 performs radioactive irradiation under the set radioactive irradiation conditions (step T2).

As radiation is emitted from the radiation source 3, energy according to the dose of radiation emitted is accumulated as electric charges by each detection element in the FPD 9, and the electric charges accumulated in the respective detection elements are read out. Thus, image data (RAW data) of a medical image is generated and stored in the storage section (step T3).

Next, in the FPD 9, the controlling part reduces a medical image stored in the storage part and a preview image is generated (step T4). The preview image is a reduced version of a medical image. To be specific, a preview image made of pixels at given pixel intervals is generated by thinning out the medical image at a predetermined percentage. The image data of the generated preview image is transmitted to the imaging console 5 either through the bucky device or wireless communication (step T5). Thereafter, the image data of the medical image stored in the storage part is transmitted to the imaging console 5 either through the bucky device or wireless communication (step T6). The image data of the preview image and the medical image which have been received in the imaging console 5 through a communication I/F 55 is stored in the storage section 52.

In the imaging console 5, once the image data of the preview image is received through the communication I/F 55, correction processing and image processing are performed on the preview image (step T7). At step T7, correction processing such as offset correction processing, gain correction processing, defective pixel correction processing, and lag correction processing is executed as necessary using the aforementioned dark image based on characteristic information of the FPD 9 stored in the storage section 52. Also, gradation processing, frequency enhancement processing, and graininess suppression processing are executed as image processing depending on an imaged region.

When there is more than one FPDs 9, the characteristic information thereof may be stored in the storage section 52 in correspondence with IDs of the respective FPDs 9, the ID may be obtained from the FPD 9 through the bucky device to be used, and the correction processing and the image processing may be executed based on the characteristic information which correspond to the obtained ID.

Figure 21:
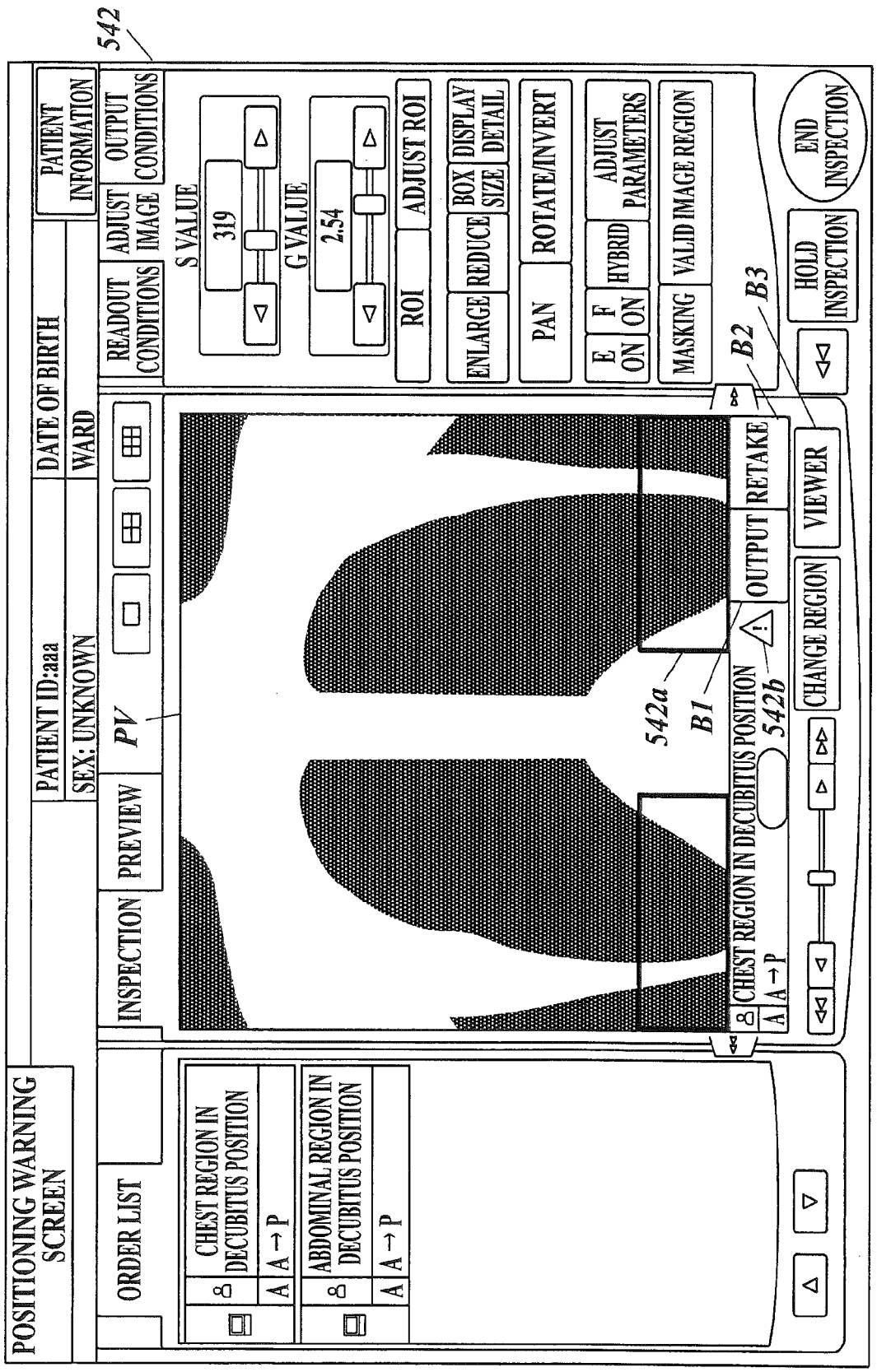
FIG. 21 is a view showing an example of a positioning warning screen.

Next, an image confirmation screen showing the preview image is displayed on the display section 54 (step T8). The image confirmation screen displayed at step T8 is a screen on which the preview image is displayed and, although not illustrated, an enlarged image display box 542a and a mark 542b in a positioning warning screen 542 illustrated in FIG. 21 are not displayed. The rest of the screen layouts and buttons displayed are the same as those of the positioning warning screen 542.

Here, whether the medical image is suitable for diagnosis by a medical doctor is judged based on, for example, appropriateness of positioning, existence of motions, adequacy of a radiation dose, and validity of image processing conditions. However, since the preview image is inferior to a diagnostic medical image in resolution and image quality, an image which requires a retake due to inappropriate positioning and motions may be overlooked. When an operator tries to confirm a preview image even more carefully in order to reduce the risk of overlooking inappropriate images, more time is needed for the confirmation, thus causing a large burden on a patient as he/she needs to hold the positioning longer.

Therefore, at step T9, the image judging process is executed in order to judge whether a medical image captured is an image which meets predetermined criteria for a medical image used for diagnosis (an image which satisfies the criteria as a diagnosis medical image) by analyzing the preview image (step T9). Here, as the image judging process at step T9, any of a positioning judging process, a motion judging process, a radiation dose judging process, and a judging process for image processing conditions explained below, or a combination thereof is executed. It should be noted that, in the following description regarding each of the processes, a case will be explained where a preview image of a lung field is used as an example. However, the same method may be used for the image judging process for other imaged regions.

First, the positioning judging process will be explained. FIG. 17 shows a flowchart of the positioning judging process. The positioning judging process is a process for judging whether there is any defect in a specific region in a medical image captured, and, when there is a defect in the specific region, it is judged that the positioning is bad and a warning is provided. The positioning judging process is executed in collaboration of the controlling section 51 and the programs stored in the storage section 52.

First of all, a process is conducted for recognizing a range of irradiation field in the preview image (step T201). In this process, a portion in an imaging area of the FPD 9 is detected where radiation from the radiation source 3 did not reach during image capture due to masking, the detected portion is removed from the preview image, and the remaining portion of the preview image is set as the irradiation field. The process for setting the irradiation field can be executed by means of, for example, detecting a region in which the signal values of pixels are almost lowest (in other words, a region where radiation doses are the lowest) continuously from the outline of the image towards the inner side thereof, and removing such region from the image.

Figure 18A:
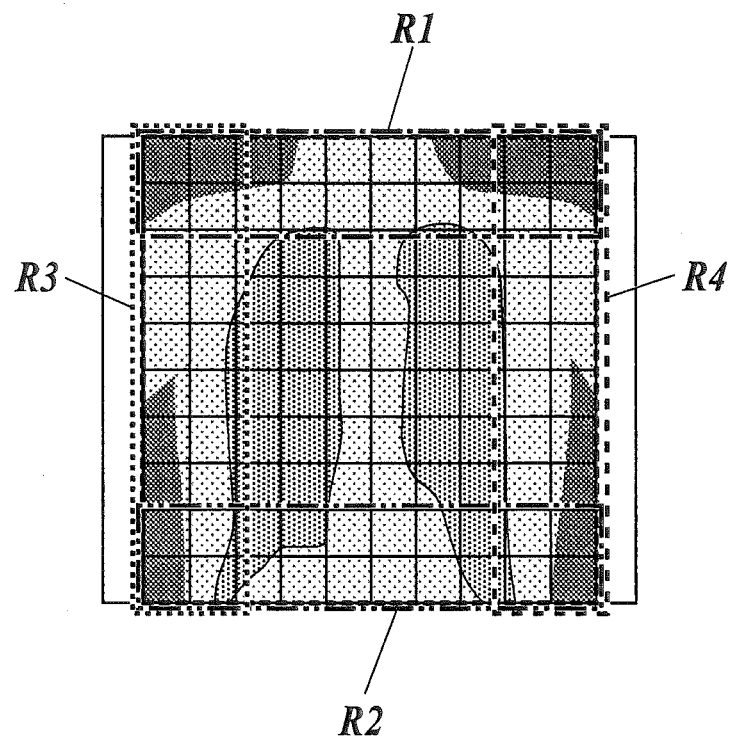
FIG. 18A is a view for explaining partial regions in the vicinities of the borderlines of an irradiation field.
Figure 18B:
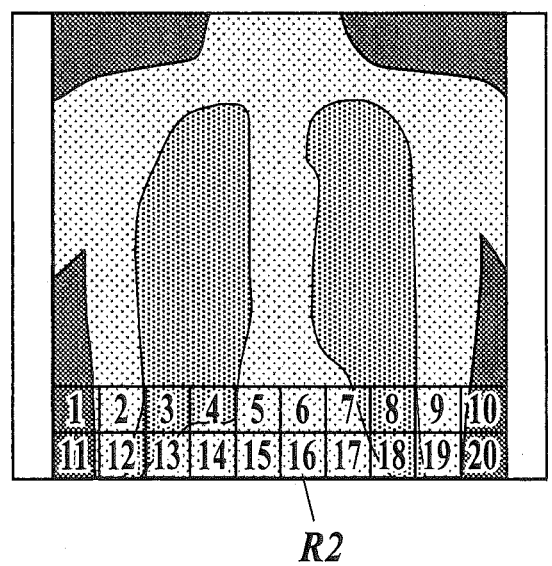
FIG. 18B is a view for explaining small regions from which feature values are calculated.

Next, the identified irradiation field is divided into small regions. Among the plurality of small regions, predetermined feature values are extracted from the small regions which are included in a partial region in a given range from the border of the irradiation field (a border between the irradiation field and outside thereof) (step T202). Specifically speaking, in the process at step T202, the irradiation field is divided into small regions which, for example, are arrayed in a 10×10 matrix form as illustrated in FIG. 18A. Then, feature values are extracted from signal values of the respective small regions included in the four partial regions. The four partial regions are two rows from the top and bottom borderlines of the irradiation field, and two columns from the left and right borderlines of the irradiation field (a top end region R1, a bottom end region R2, a left end region R3, and a right end region R4 in FIG. 18A). Concretely speaking, since the bottom end region R2 of FIG. 18A includes 1 to 20 small regions shown in FIG. 18B, 20 feature values are calculated. The calculation results are held as a data array which represents positions and feature values of the respective small regions. The same is applied to the upper end region R1, the left end region R3, and the right end region R4. The feature values calculated at step T202 are herein referred to as data array feature values.

Here, the partial regions in the vicinities of the borderlines may be divided into a plurality of rows or columns instead of one row or one column only, so image judgment can be done accurately even for an image with an complex pattern. It is considered that an image is complex when, for example, gas is captured at a position even lower than the bottom end of the lung field, there is fluid retention at the bottom end of the lung field, or a catheter is inserted near the bottom end of the lung field. In such cases, judgment can be performed properly by using the judging unit 51a which has done learning based on the data of the small regions in the plurality of rows and columns.

The feature values extracted in the process of step T202 are, for example, maximum values of the signal values (in other words, the highest intensities of measured radiation) held by the respective pixels in the respective small regions. Also, other feature values may be maximum values of the first derivatives of signal values in the respective small regions, or, maximum values among the first derivatives of the signal values in the respective small regions especially in components parallel to the borderlines of the irradiation field, as well as coordinate values of these maximum values of the first derivatives. Alternatively, power spectrum of luminance values may also be used as the feature values. In particular, power spectrum densities in directions parallel to the borderlines of the irradiation field, and frequency (wavelength) values which reaches a maximal value may be used.

After the foregoing feature values are extracted, positioning is judged for each borderline (step T203). The positioning judgment at step T203 is performed by using the judging unit 51a to judge whether the subject includes a missing portion due to the borderlines. In the example shown in FIG. 18A, the feature values calculated at step T202 are obtained from the upper end region R1, the bottom end region R2, the left end region R3, and the right end region R4. These feature values are inputted to the judging unit 51a of the controlling section 51, and it is judged in the judging unit 51a whether the lung field includes any portion outside the borderlines and missing.

The judging unit 51a used for this positioning judgment has already done learning using a given learning algorithm and judges whether any portion of the lung field is outside each of the borderlines and missing.

Here, general concepts of learning and judgment by using a learning algorithm will be explained. In order to simplify the description, an example will be explained where two types of feature values are used for judgment.

Figure 19:
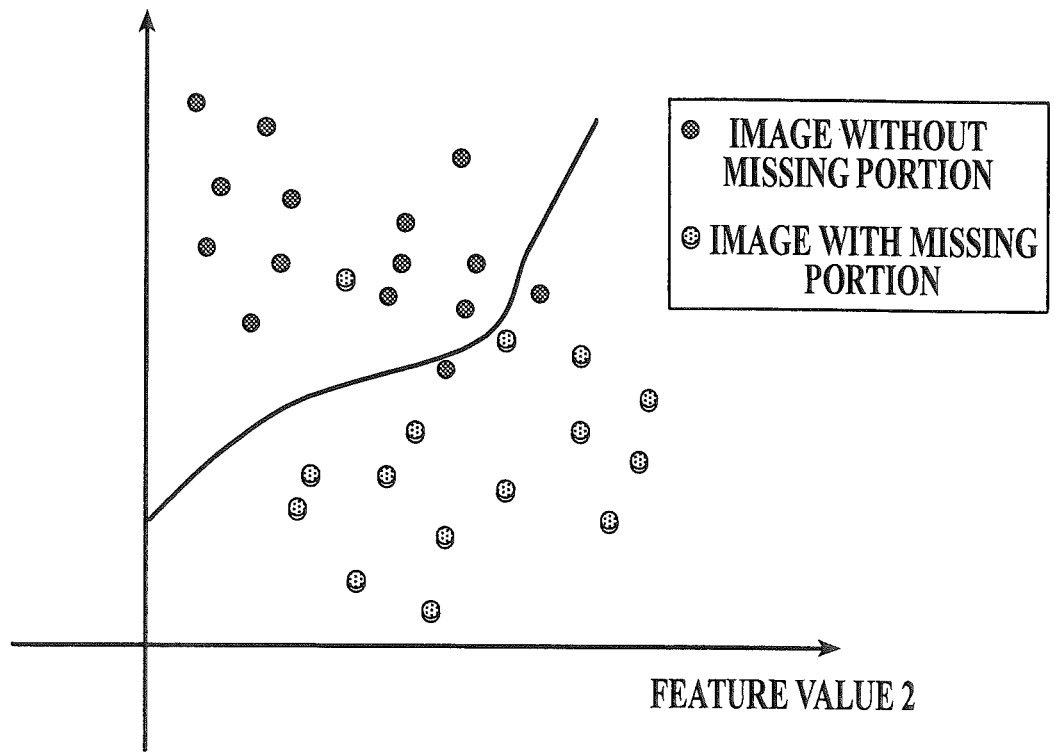
FIG. 19 is graph showing feature values calculated from a plurality of images (sample images) in which existence of a missing portion in the lung field is already known, and the feature values are plotted in a space having axes which represent respective types of feature values which are used for the positioning judgment.

FIG. 19 is a graph which shows feature values plotted in a space where the respective types of feature values used for the positioning judgment are used as axes, respectively, and, the plotted feature values have been calculated from a plurality of images (samples images) in which whether there is any missing portion in the lung field is already known. As evident from FIG. 19, with the learning algorithm, such a judging unit is formed that learns how the borderlines should be drawn to distinguish an image having a missing portion in the lung field from an image having no missing portion in the lung field, based on a feature value distribution calculated from the plurality of sample images, and judges whether an image includes a missing portion or not depending on which side of the borderline a feature value is located. Then, by inputting the feature values calculated from an image to be judged by the judging unit formed, it is judged at the judging unit whether the image includes any missing portion in the lung field.

Examples of a learning algorithm used for the judging unit 51a for learning includes, but not specifically limited to, AdaBoost. AdaBoost is an algorithm which prepares a number of data arrays of a plurality of feature values extracted from images in which whether there is a missing portion in a subject is already known, and forms an optimum judging unit by weighting and combining discriminators which judges existence of missing portion in the subject.

Here, formation of the judging unit 51a based on learning, and the judgment at step T203 will be explained using an exemplary case where the AdaBoost is used.

At step T203, the positioning judgment is carried out for each of the top, bottom, left and right borderlines of the irradiation field. The judging unit 51a includes four types of judging units, which are an upper end judging unit, a lower end judging unit, a left end judging unit, and a right end judging unit.

(1) First, in forming the judging unit 51a, a plurality of images is prepared as sample images with and without a missing portion in the lung field.

(2) Next, feature values that are similar types to those obtained at step T202 are calculated from all of the sample images. For example, calculated are feature values of signal values (for example, maximum signal values) in the respective small regions included in each of the four partial regions, that is, the upper end region R1, the bottom end region R2, the left end region R3, and the right end region RA illustrated in FIG. 18A.

Thereafter, for each of the upper end region R1, the bottom end region R2, the left end region R3, and the right end region R4, the processes (3) through (4) explained below are executed using the calculated feature values. Thus, the upper end judging unit, the bottom end judging unit, the left end judging unit, and the right end judging unit are formed.

FIGS. 20A to 20D are views which schematically illustrate a forming process of the bottom end judging unit. The graphs shown in FIGS. 20A to 20D are two-dimensional feature value distributions where the vertical axis represents a feature value 1 and the horizontal axis represents a feature value 2. Although the description will be given with a two-dimensional expression using two types of feature values for simplification, the feature value space is twenty-dimensional with twenty axes in reality, because there are twenty of data array feature values. The description below will be provided with reference to FIGS. 20A to 20D which schematically shows the forming process of the bottom end judging unit. However, the same forming process is applied to the upper end judging unit, the left end judging unit, the right end judging unit.

(3) First of all, a plurality of weak discriminators is formed by using a decision stump. The weak discriminators judge existence of a missing portion in the lung field based on whether a certain feature value exceeds a determined threshold value. More than one discriminator is formed with different threshold values for each type of the feature value.

Figure 20A:
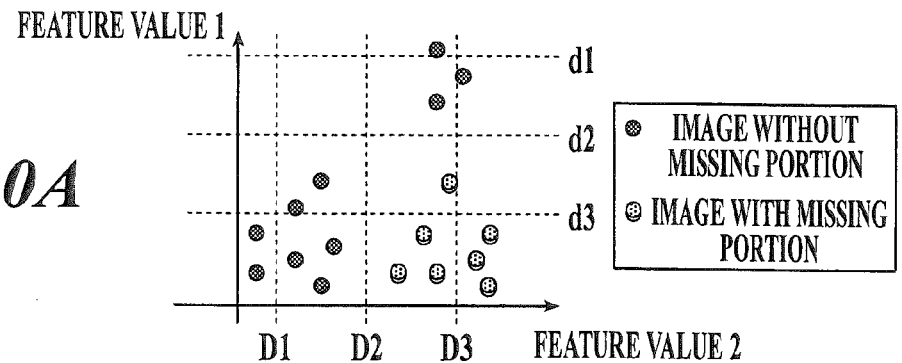
FIG. 20A is a view schematically showing a process of creating a lower end discriminator (a first step)

For example, as shown in FIG. 20A, three weak discriminators having different threshold values d1, d2, and d3 are formed for the feature value 1, and three weak discriminators having different threshold values D1, D2, and D3 are formed for the feature value 2.

Figure 20B:
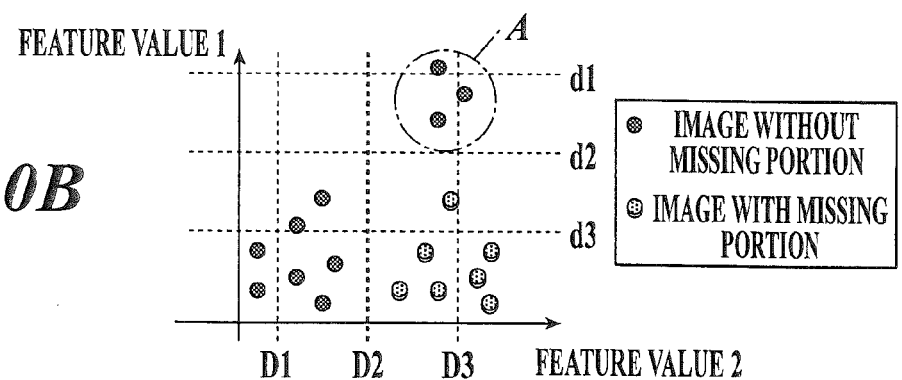
FIG. 20B is a view schematically showing the process of creating the lower end discriminator (a second step)

(4) Then, a weak discriminator is selected which contributes most to the judgment whether there is a missing portion in the lung field. For example, as shown in FIG. 20B, the weak discriminator D2 is able to make correct judgment for 14 images except for three images enclosed by a circle A, and has the highest percentage (or number) of the correctly-judged images (that is, the contribution percentage is the highest). Therefore, the weak discriminator D2 is selected as the one which contributes most to judgment of existence of a missing portion in the lung field.

Figure 20C:
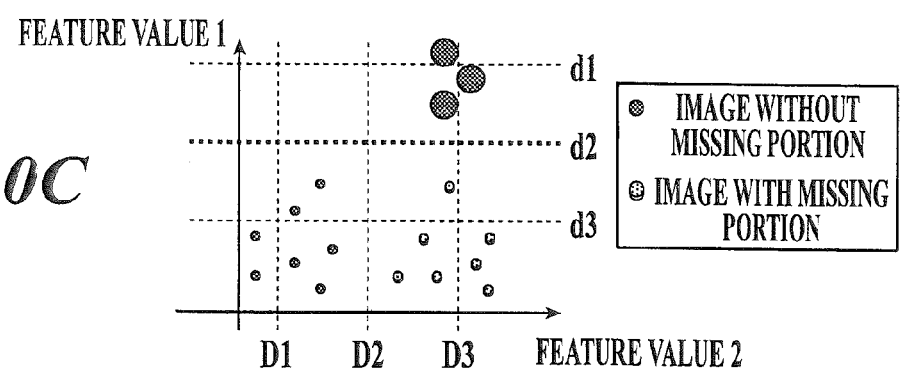
FIG. 20C is a view schematically showing the process of creating the lower end discriminator (a third step)

(5) Next, by weighting the feature values of the images which were falsely judged, a weak discriminator is selected which contributes most to the judgment of existence of a missing portion in the lung field. Since incorrectly-judged images are weighted, it becomes possible to select a weak discriminator which can accurately judge images which were falsely judged by the weak discriminator D2. For example, as shown in FIG. 20C, when weighting of the images that were judged incorrectly in FIG. 20B (the images that correspond to the points surrounded by the circle A) is increased, and the weighting of the rest of the images is reduced, the contribution percentage of the weak discriminator d2 becomes the highest. As a result, the weak discriminator d2 is selected.

Figure 20D:
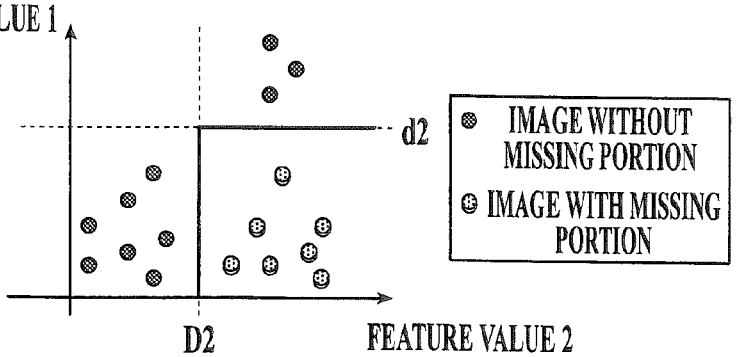
FIG. 20D is a view schematically showing the process of creating the lower end discriminator (a fourth step)

(6) The process (5) is repeated until no image is incorrectly judged, and the judging unit is formed by combining weak discriminators selected in each of the processes. In FIG. 20D, the judging unit is formed by combining the weak discriminators D2 and d2. Having said that, since each of the weak discriminators has a different contribution percentage, weighting is carried out based on the percentage of correct answers (the percentage of correctly-judged images out of all of the images) of each of the weak discriminators.

At step T203, it is judged whether there is any missing portion in the lung field in the top, bottom, left and light ends of the lung field in a captured medical image by using the judging unit 51a formed of the judging units (four judging units on the top, bottom, left and right) which are created in the aforementioned learning process. Specifically, the feature values respectively calculated from the top end region R1, the bottom end region R2, the left end region R3, and the right end region R4 are inputted in the top end judging unit, the bottom end judging unit, the left end judging unit, and the light end judging unit, respectively. Then, the judging unit 51a judges whether there is a missing portion in the lung field on the top, bottom, left and right borders of the irradiation field.

Alternatives of applicable learning algorithms include those using a support vector machine or a neutral network, or a K-nearest neighbor classifier. A statistical approach such as discriminant analysis may be applied as well (reference: C. M. Bishop, "Pattern Recognition and Machine Learning", Springer-Verlag, new edition, 2006). Meanwhile, the support vector machine is a statistical algorithm which maps data points expressed by combinations of the plurality of feature values (feature vectors) extracted in the process at step T202 to the higher-dimensional space, and evaluates a separation plane which linearly separates images with and without missing portions in a specific region in the mapped higher-dimensional space most accurately, in other words, with the largest margin therebetween.

When the result of the positioning judgment shows that the captured medial image has a missing portion in a specific region (or positioning is bad) (step T204: YES), a positioning warning screen 542 is displayed on the display part 54 (step T205).

FIG. 21 shows an example of the positioning warning screen 542. As shown in FIG. 21, in the positioning warning screen 542, a box 542b which indicates a missing portion of the image is displayed on the preview image PV in an overlapping fashion. Also, the mark 542b is displayed indicating that there is a warning. In addition, an output button B1, a retake button B2, and a viewer button B3 are displayed on the positioning warning screen 542. The output button B1 provides an instruction to output and save the medical image which corresponds to the displayed preview image PV in the server device 10 as a medical image for diagnosis. The retake button B2 provides an instruction to discard the medical image corresponding to the displayed preview image PV and have a retake. The viewer button B3 provides an instruction to execute correction processing and image processing on the medical image corresponding to the preview image PV and create a medical image for diagnosis.

After the positioning judging process, another image judging process is executed or the process moves on to the step T10 shown in FIG. 16.

Figure 22:
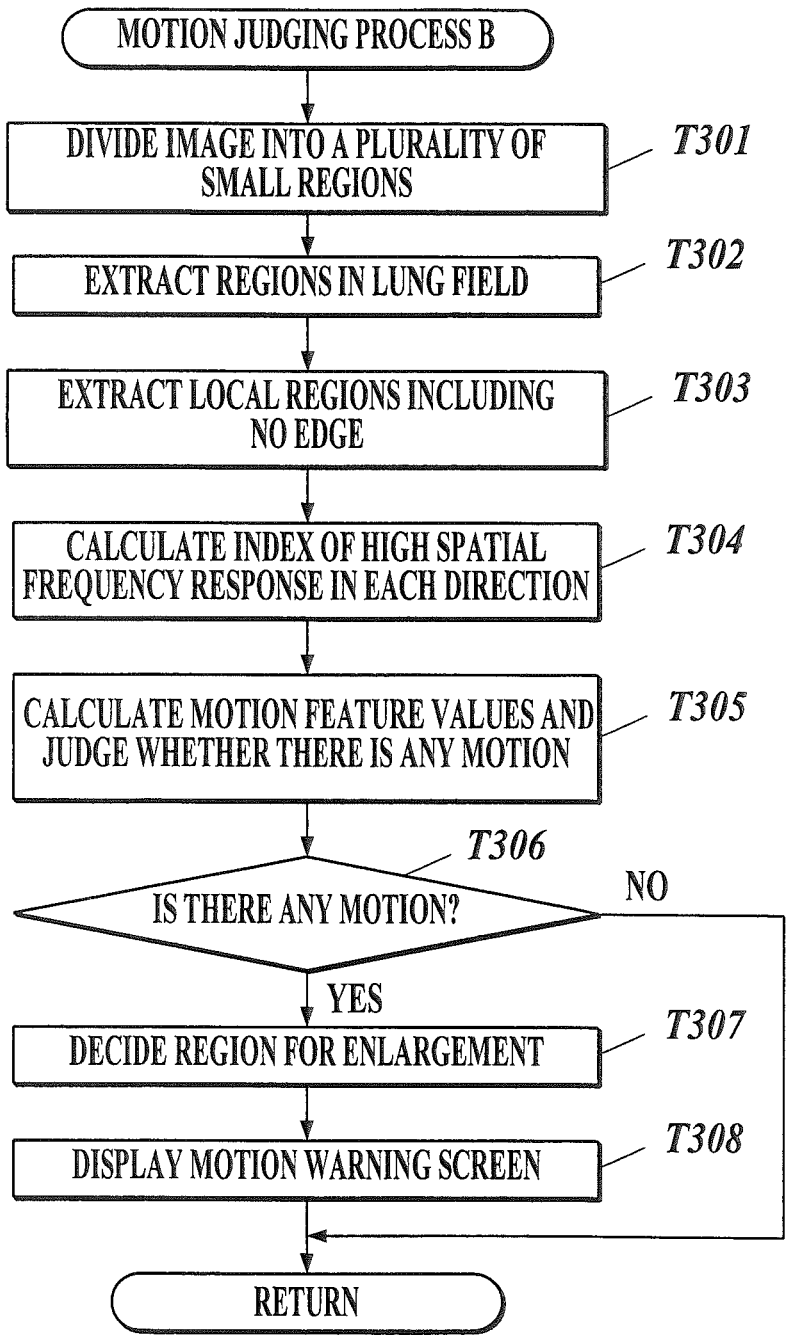
FIG. 22 is a flowchart showing a motion judging process B which is an example of an image judging process executed at step T9 shown in FIG. 16.

Next, the motion judging process B will be explained. FIG. 22 shows a flowchart of the motion judging process B. The motion judging process is a process for judging whether there is any motion in a subject in a captured medical image based on a preview image, and providing a warning when it is judged that there is a motion in the subject. The motion judging process B is executed in collaboration of the controlling section 51 and the programs stored in the storage section 52.

An algorithm for the motion judging process B shown in FIG. 22 is similar to the one explained with reference to FIGS. 5A to 5C and FIG. 6 in the first embodiment, so the same description thereof is applied hereto.

Also, processes in steps T301 to T305 executed on the preview image in the motion judging process B are similar to those in steps S101 to S105 executed on a medical image in the motion judging process shown in FIG. 4. Therefore, the same explanation is applied thereto.

As a result of the judgment carried out at steps T301 to 305 regarding existence of a motion, when it is judged that there is a motion in the subject in the captured medical image (step T306; YES), a region for enlargement is decided in order to display an enlarged part of a motion, based on positional information and high spatial frequency components of the local region without edges (step T307). The process for deciding a region for enlargement at step T307 is similar to the one explained in the first embodiment with reference to FIGS. 13A to 13C. Therefore, the same explanation is applied hereto.

Next, the display section 54 displays a motion warning screen 543 in which the decided enlargement region is enlarged and displayed (step T308).

Figure 23:
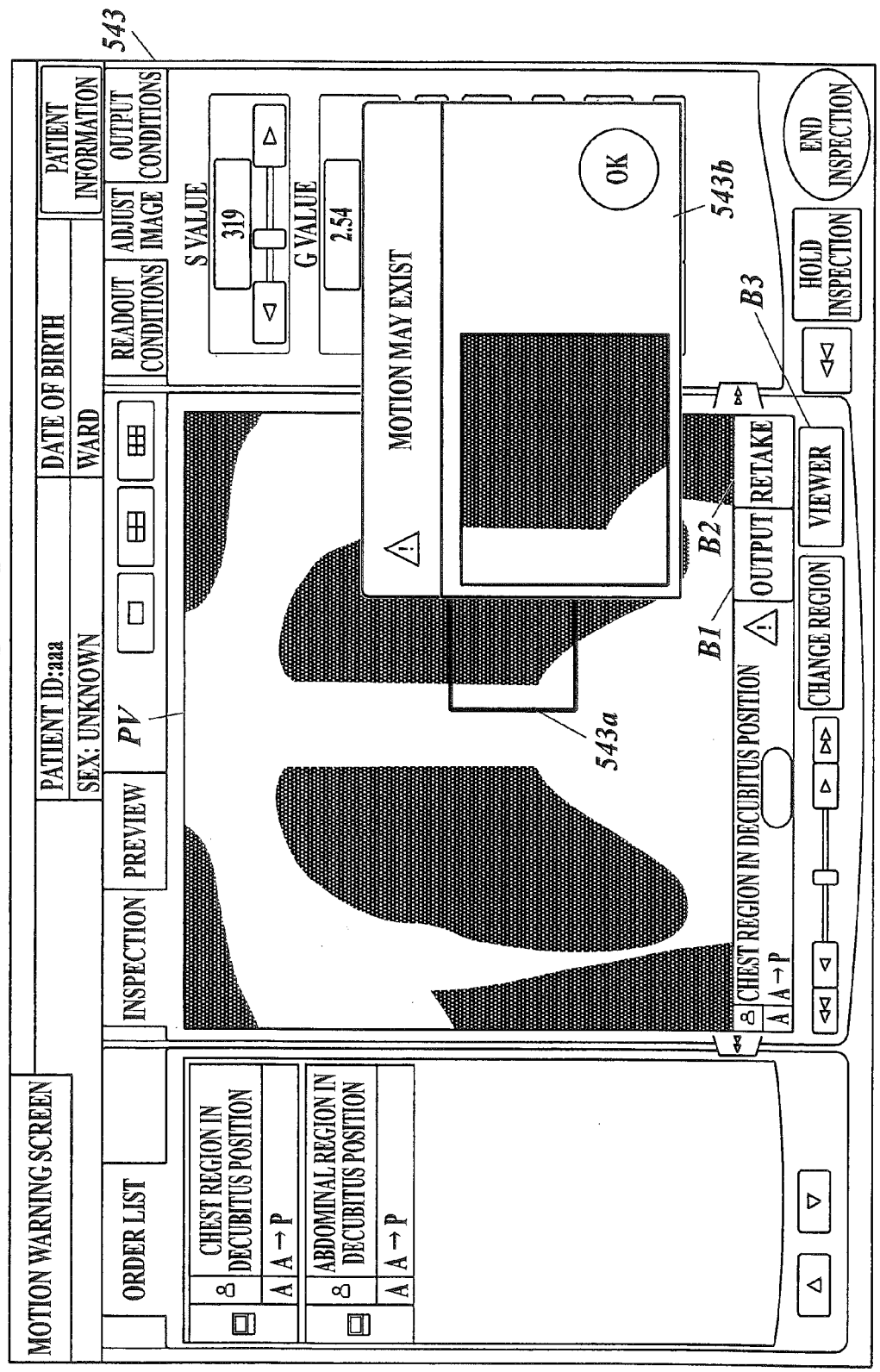
FIG. 23 is a view showing an example of a motion warning screen which is displayed at step T308 in FIG. 22.

FIG. 23 shows an example of the motion warning screen 543. In the motion warning screen 543, a box 543a which indicates the enlargement region decided as above is displayed in an overlapping fashion on the preview image PV. At the same time, the screen 543b pops up which displays an enlarged image of the above-mentioned enlargement region and a warning message such as "motion may exist". In addition, an output button B1, a retake button B2, and a viewer button B3 are displayed on the motion warning screen 543. The output button B1 provides an instruction to output and save the medical image which corresponds to the displayed preview image PV in the server device 10. The retake button B2 provides an instruction to discard the medical image corresponding to the displayed preview image PV and have a retake. The viewer button B3 provides an instruction to execute correction processing and image processing on the medical image corresponding to the preview image PV and create a medical image for diagnosis.

After the motion judging process, another image judging process is executed or the process moves on to the step T10 shown in FIG. 16.

Figure 24:
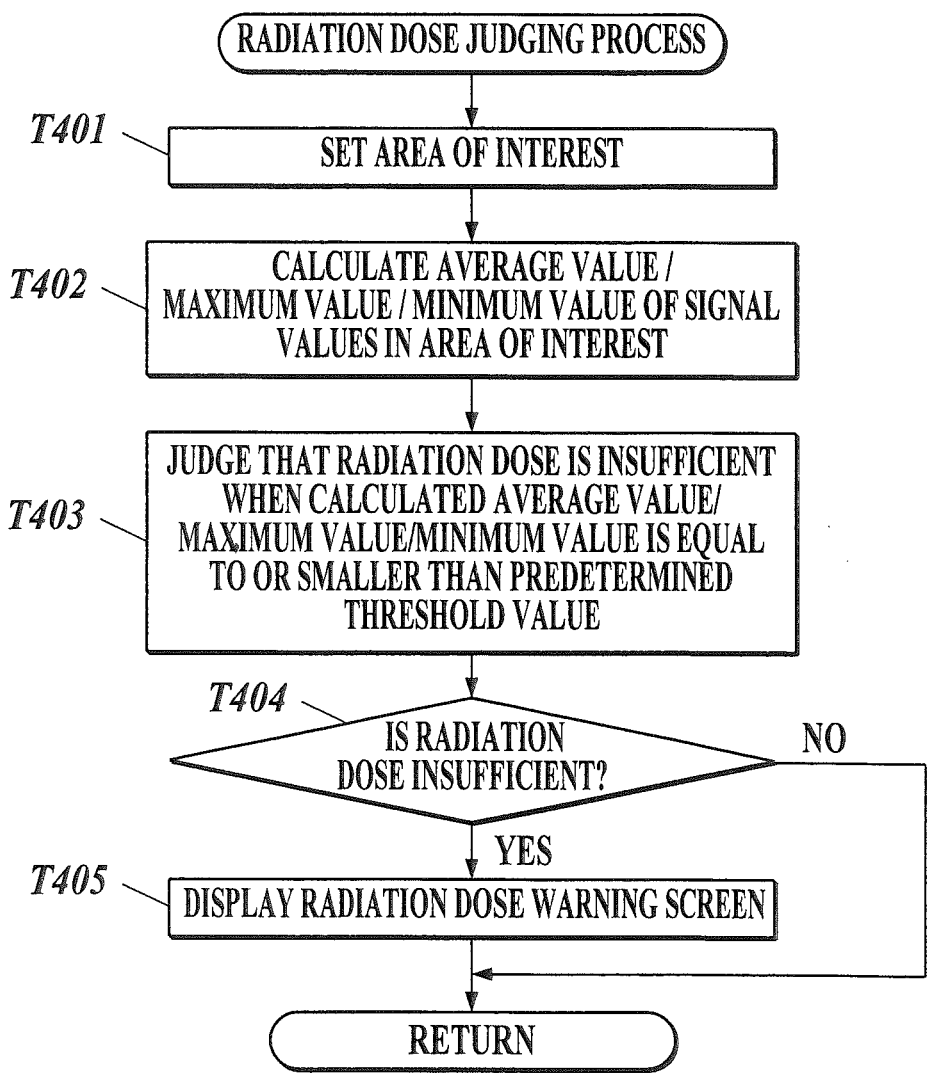
FIG. 24 is a flowchart showing a radiation dose judging process which is an example of the image judging process executed at step T9 in FIG. 16.

Next, a radiation dose judging process will be explained. FIG. 24 shows a flowchart of the radiation dose judging process. The radiation dose judging process judges whether an amount of radiation emitted while capturing a medial image exceeds a predetermined reference value, and provides a warning when it is judged that the amount of radiation does not exceed the reference value (the dose is insufficient). The radiation dose judging process is executed in collaboration of the controlling section 51 and the programs stored in the storage section 52. The radiation dose judging process is executed based on a preview image before correction processing and image processing.

First of all, a preview image before correction processing and image processing stored in the storage section 52 is read out, and an area of interest is set (step T401). In an image of front chest, a rectangular area including the lung field is set as the area of interest. For example, the lung field is extracted by the method explained earlier, and a rectangular area which encloses the outer side of the extracted lung field is set as the area of interest.

Then, an average value, a maximum value, or a minimum value of signal values of the pixels in the area of interest is calculated (step T402).

Thereafter, the calculated average value, maximum value, or minimum values is compared to a predetermined threshold value which is previously set for each of the above values. When the value is greater than the threshold value, it is determined that the radiation dose is over the predetermined reference value. When the calculated average value, maximum value, or minimum value is equal to or smaller than the threshold value which is set for each of the values in advance, it is determined that the radiation dose is not over the predetermined reference value, which means that the radiation dose is insufficient (step T403).

Each of the average value, maximum value, and minimum value of signal values of pixels in the area of interest may be compared to the threshold value that are previously set for each of the values, and it may be judged that a radiation dose is insufficient when any of the values is equal to or smaller than the corresponding threshold value.

When it is determined that radiation dose is not sufficient (step T404; YES), a radiation dose warning screen 544 is displayed on the display section 54 (step T405).

Figure 25:
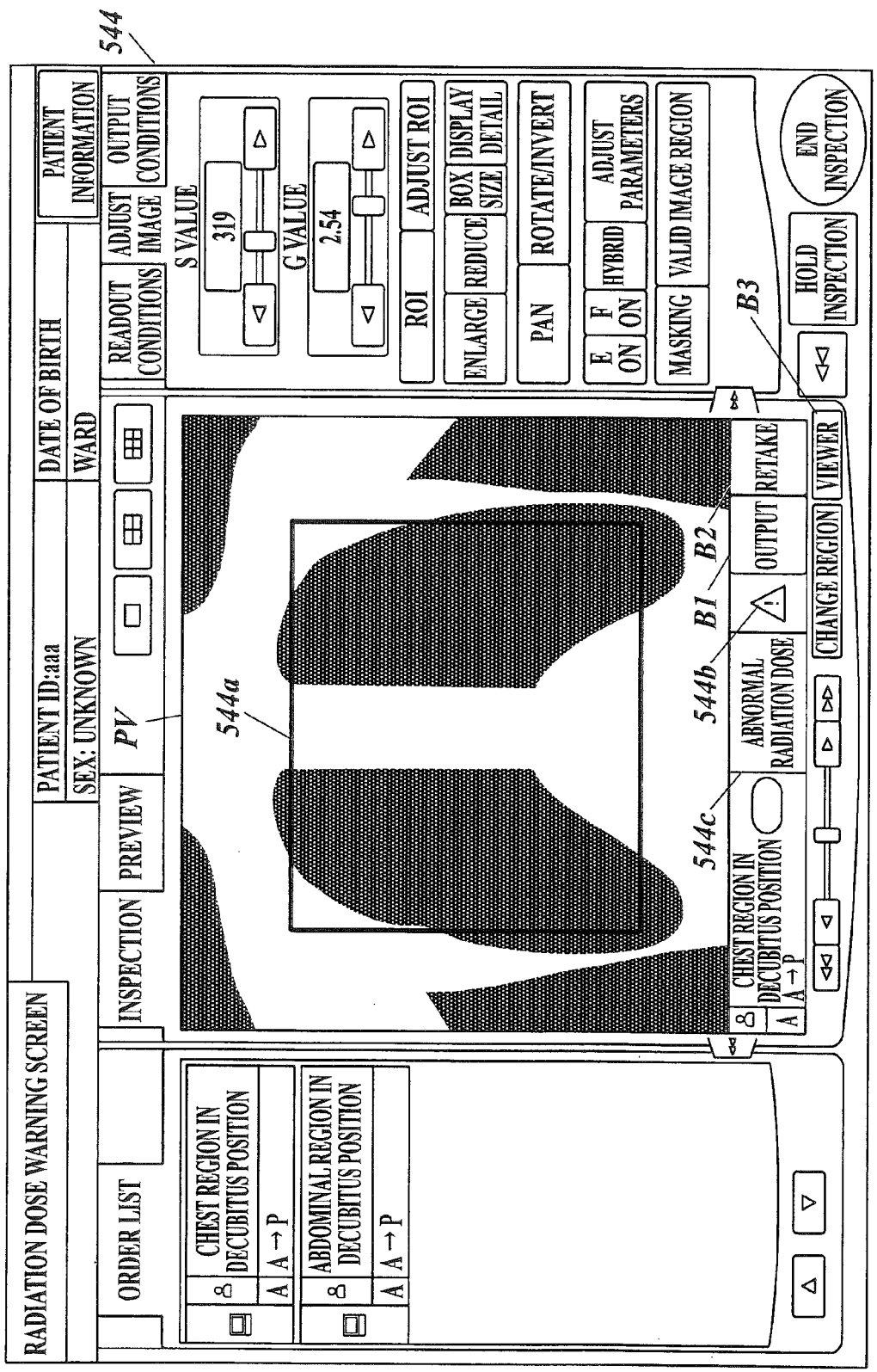
FIG. 25 is a view showing an example of a radiation dose warning screen.

FIG. 25 shows an example of the radiation dose warning screen 544. In the radiation warning screen 544, a box 544*a* which indicates the area of interest set as explained above is displayed in an overlapping fashion on the preview image PV. At the same time, a mark 544*b* which indicates existence of abnormality, and a warning message 544*c* that says "abnormal radiation dose" are displayed. In addition, an output button B1, a retake button B2, and a viewer button B3 are displayed on the radiation dose warning screen 544 The output button B1 provides an instruction to output and save the medical image displayed in the server device 10. The retake button B2 provides an instruction to discard the medical image corresponding to the displayed preview image PV and have a retake. The viewer button B3 provides an instruction to execute correction processing and image processing on the medical image corresponding to the preview image PV and create a medical image for diagnosis.

After the radiation dose judging process, another image judging process is executed or the process moves onto the step T10 shown in FIG. 16.

Figure 26:
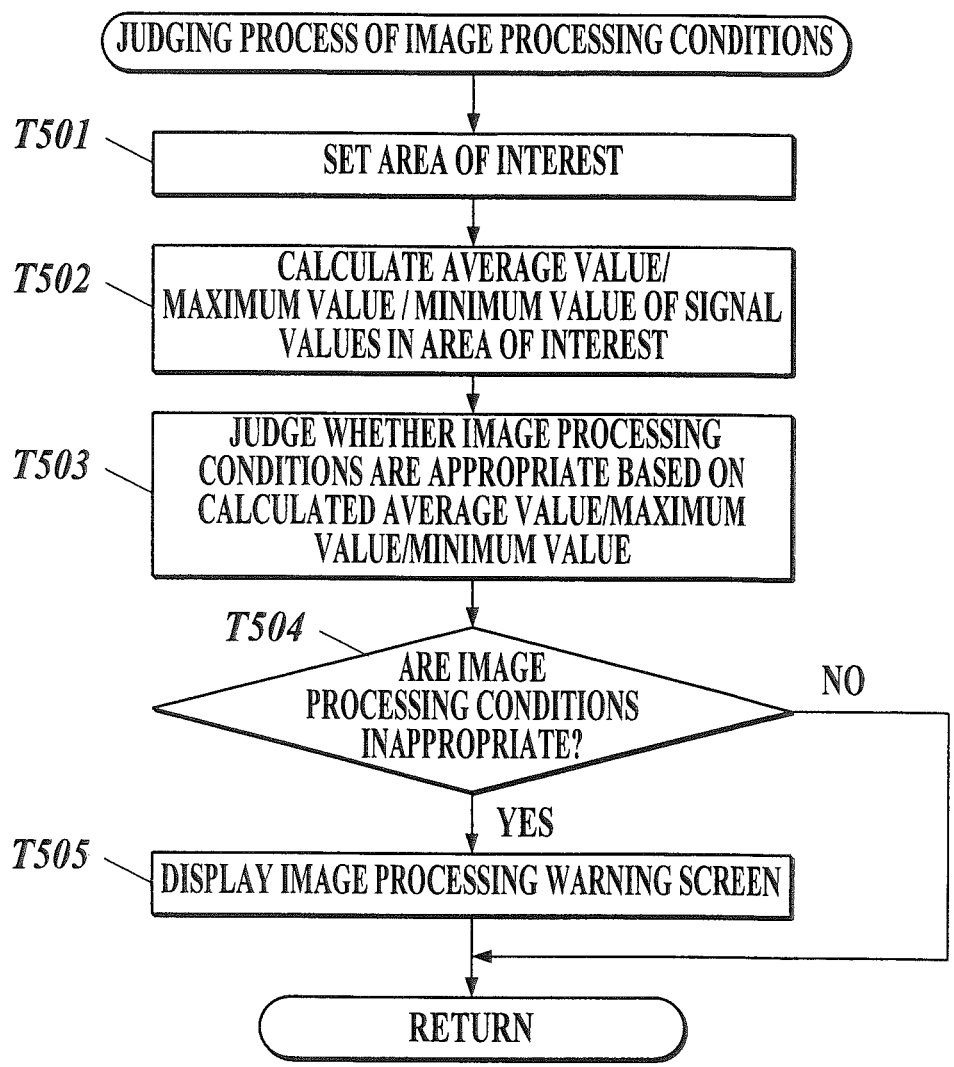
FIG. 26 is a flowchart showing a judging process of image processing conditions which is an example of the image judging process executed at step T9 in FIG. 16.

Next, the judging process for image processing conditions will be explained. FIG. 26 shows a flowchart of the judging process for image processing conditions. The judging process for image processing conditions judges whether conditions f or image processing executed on a captured medical image are appropriate based on the conditions of image processing executed on the preview image, and provide a warning when it is judged that the conditions are not appropriate. The judging process for image processing conditions are executed in collaboration of the controlling section 51 and the programs stored in the storage section 52.

First, an area of interest is set in the preview image (step T501). In an image of the front chest, a rectangular area including the lung field is set as the area of interest. For example, the lung field region is extracted by the method explained earlier, and a rectangular area which encloses the outer side of the extracted lung field region is set as the area of interest.

Then, an average value, a maximum value, and a minimum value of signal values of pixels in the area of interest are calculated (step T502).

Thereafter, the calculated average value, maximum value, and minimum value are compared to predetermined threshold values which are set for the respective values in advance. Based on the results of the comparison, it is judged whether the conditions of image processing executed on the captured medical image are appropriate (step T503).

Here, it is mainly judged whether conditions for gradation processing are appropriate as image processing conditions. When the calculated average value and maximum value are greater than the predetermined threshold values, it is judged that the image processing conditions are not appropriate because, for example, signals in the lung field are blacked out. When the calculated minimum value is smaller than the predetermined threshold value, it is judged that the image processing conditions are inappropriate because the hear region is turned white-out.

When it is judged that the image processing conditions are inappropriate (step T504; YES), the image processing warning screen 545 is displayed on the display part 54 (step T505).

Figure 27:
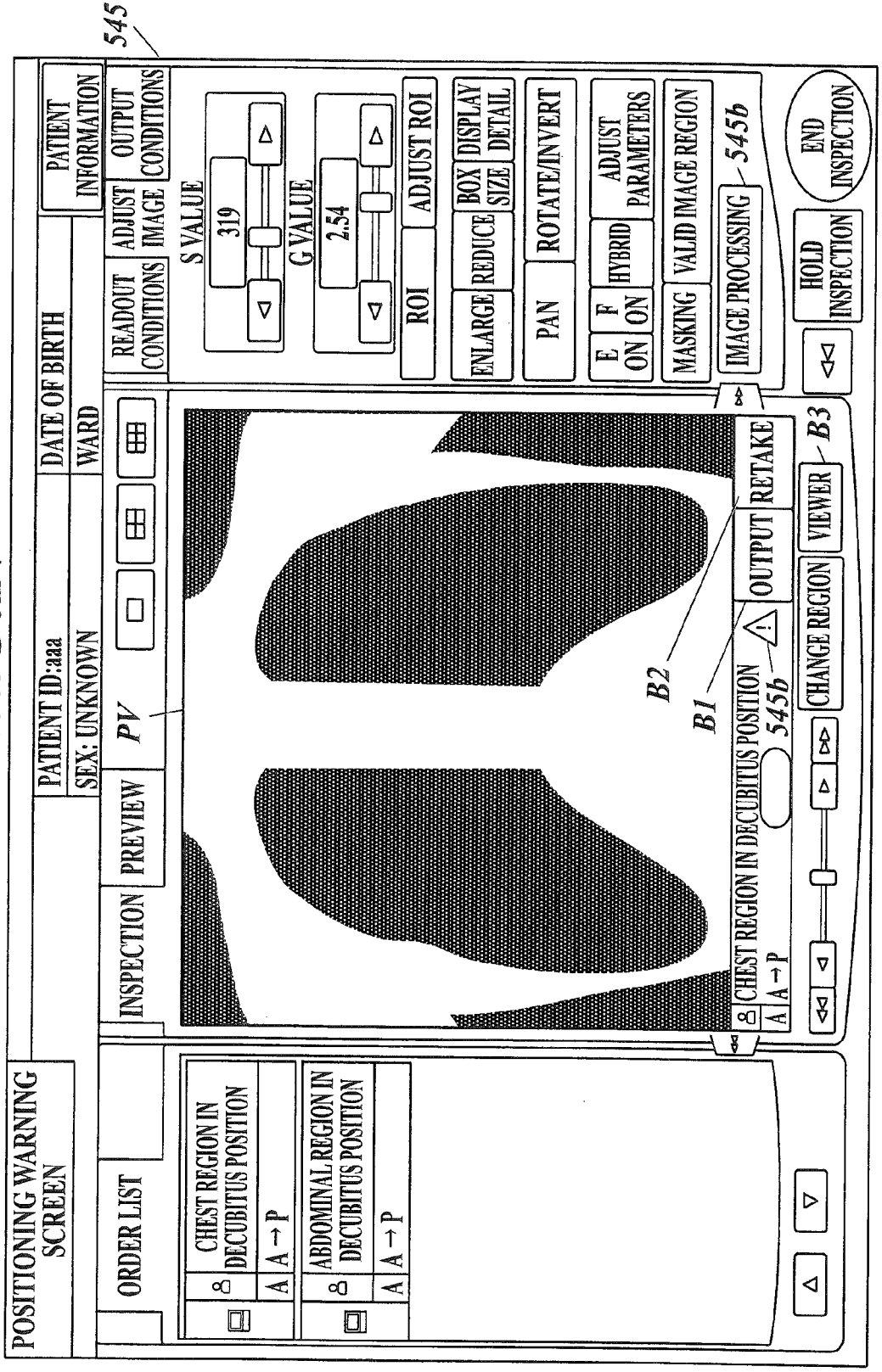
FIG. 27 is a view showing an example of an image processing warning screen.

FIG. 27 shows an example of the image processing warning screen 545. The image processing warning screen 545 displays a mark 545*a* which indicates that image processing conditions are not appropriate, and a message 545*b* which notifies that "image processing" is not properly done. In addition, an output button B1, a retake button B2, and a viewer button B3 are displayed on the image processing warning screen 545. The output button B1 provides an instruction to output and save the medical image corresponding to the displayed preview image PV in the server device 10. The retake button B2 provides an instruction to discard the medical image corresponding to the displayed preview image PV and have a retake. The viewer button B3 provides an instruction to execute correction processing and image processing on the medical image corresponding to the preview image PV and create a medical image for diagnosis.

After the judging process for image processing conditions, another image judging process is executed or the process moves on to the step T10 shown in FIG. 16.

When the image judging process is executed as a combination of the foregoing positioning judging process, the motion judging process, the radiation dose judging process, and the judging process for image processing conditions, it is preferred that the warning screens be integrated and displayed on a single screen. Namely, it is preferred that the boxes, marks, and screens to be displayed on the respective warning screens be displayed on a single warning screen.

At step T10 shown in FIG. 16, it is judged whether the retake button B2 has been depressed in the inputting section 53. When it is judged that the retake button B2 has been depressed by the inputting section 53 (step T10; YES), a preview image to be processed and a corresponding medical image are deleted from the storage section 52 (step T11), and the process returns to step T2. On the other hand, when the retake button B2 is not depressed by the inputting section 53 (step T10; NO) and display of a diagnostic medical image is instructed by depression of the viewer button B3 (step T12; YES), the medical image stored in the storage section 52 is read out and correction processing and image processing are executed thereon, thus generating a medical image for diagnosis (step T13). Then the medical image for diagnosis is displayed on the display section 54 (step T14). The correction processing and the image processing executed are almost the same (the processing is executed under almost the same conditions) as those for the preview image. Then, once the output button B1 is depressed (step T15; YES), the image data of the medical image for diagnosis is transmitted by the network communication section 56 to the server device 10 in correspondence with the imaging order information which was specified at step S1 (step T16), and the medical image generating process ends. In the server device 10, the received image data of the medical image is stored in the database in correspondence with the imaging order information.

As explained above, the imaging console 5 judges whether a medical image meets predetermined criteria as a medical image for diagnosis (whether a medical image is suitable for diagnosis), by using a preview image which is a reduced version of a captured medical image. When it is judged that the criteria is not satisfied, the imaging console 5 displays a warning screen on the display part 54 to warn that the medical image is not suitable for diagnosis. This way, when a defective image that is not appropriate for diagnosis is captured, the warning is displayed immediately after the image is captured. Therefore, a radiographer is able to instantaneously recognize a defective image which is not suitable for diagnostic use, and a defective image is prevented from being overlooked. Moreover, when a defective image is captured, a warning is provided immediately. Therefore, time required for a radiographer to recognize a defective image is shorter than conventional visual check, and a patient needs to hold the positioning only for a short period of time. In addition, it is not necessary to release a patient from the positioning once during a time period required for an image judging process. Hence, only fine adjustments are required for imaging conditions and positioning even if a retake is needed, thus significantly reducing burdens on a radiographer and a patient.

Moreover, even in a preview image on a small console with poor resolution and image quality, an area to be confirmed is highlighted or enlarged on the preview screen. Therefore, it becomes easier to confirm the image, and time and workload required for the confirmation can be greatly reduced.

In the foregoing second embodiment, the example explained was a case where the present invention is applied to the medical imaging system 100 which is installed in the radiography room Rm. However, as described below, the present invention can also be applied to a medical imaging system 200 for a patient who has difficulty in moving.

Figure 28:
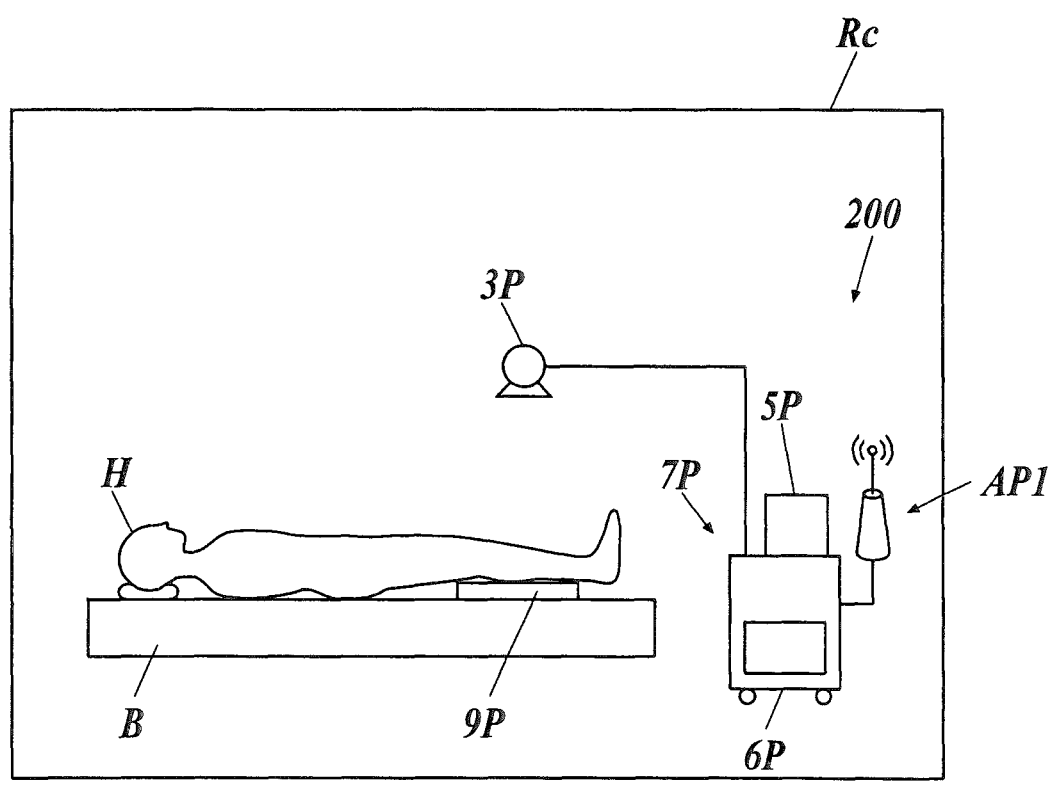
FIG. 28 is a view showing an example of a medical imaging system for a patient who has difficulty of moving.

The medical imaging system 200 is brought into a patient room Rc with the visiting car 7P as shown in FIG. 28. Then, for example, while a FPD cassette 9P is inserted between a bed B and a certain part of the body of a patient H who is lying on the bed B, radiation is emitted from a portable radiation source 3P to capture an image, and a medical image is generated.

As illustrated in FIG. 28, in the medical imaging system 200, the portable radiation source 3P and operating station 6P are mounted on the visiting car 7P, and a portable console 5P and the FPD cassette 9P are wirelessly connected to each other by an access point AP1 provided in the visiting car 7P.

The configurations and functions of the radiation source 3P, the operating station 6P, the console 5P, and FPD 9P are basically the same as those of the radiation source 3, the operating station 6, the imaging console 5, and the FPD 9 described earlier, respectively, except for their portability. The medical image generating process shown in FIG. 16 can be executed by these devices.

Specifically, at a visiting destination, an operator such as a radiographer operates an inputting section of the console 5P and displays imaging order list screen which shows a list of imaging order information on a display section. Then, by operating the inputting section, the operator specifies imaging order information of an imaging subject from the imaging order list screen.

Next, the operator inserts the FPD 9P between the bed B and a certain part of the body of the patient H lying on the bed B, and positions a subject by adjusting the position and orientation of the radiation source 3. Further, the operator sets radioactive irradiation conditions based on the imaging region and provides an instruction of radioactive irradiation from the operating stand 6P. Once the instruction of radioactive irradiation from the operating station 6P is received by the radiation source 3P, radioactive irradiation is carried out under the set radioactive irradiation conditions.

In the FPD 9P, once radiation is emitted from the radiation source 3P, energy in accordance with emitted radiation dose is accumulated by respective detection elements as electric charges, and the electric charges accumulated in these detection elements are read out and image data (RAW data) of a medical image is thus generated and stored in a storage section.

Then, in the FPD 9P, a reduced image (a preview image) is generated by a controlling section from the medical image stored in the storage section. The image data of the generated preview image is transmitted to the console 5P through wireless communication. Thereafter, the image data of the medical image stored in the storage section is transmitted to the console 5P through wireless communication.

In the console 5P, once image data of the preview image and the medical image is received, the received image data of the preview image and the medical image is stored in the storage section. Then, correction processing and image processing are executed on the preview image. The correction processing and image processing are the same as those explained in the foregoing description.

Thereafter, the display section of the console 5P displays an image confirmation screen on which the preview image is shown. Also, an image judging process is executed where the preview image is analyzed and it is judged whether the captured medical image is appropriate as a medical image for diagnostic use. As the image judging process, any of the positioning judging process, the motion judging process, the radiation dose judging process, and the judging process for image processing conditions, or a combination thereof is executed as described earlier. When it is judged that the medical image is not suitable for diagnosis, a warning screen which indicates the judgment result is displayed on the display section of the console 5P. The warning screen displayed on the console 5P is a screen shown in FIG. 21, 23, 25, or 27, and is able to highlight or enlarge a missing portion or a portion including a motion in the image.

There has been a problem in a portable console that it is more difficult to check an image compared to an installed console because the screen is small for portable convenience.

Nevertheless, with the console 5P, whether a medical image captured is appropriate for diagnostic use is judged by using a preview image which is a reduced version of the medical image, and, when it is judged that the medical image is not appropriate for diagnostic use, the warning screen which shows the judgment result is displayed on the display section. Therefore, even with a small screen for visiting, a radiographer is able to instantaneously recognize a defective image which is inappropriate for diagnosis, thus preventing a defective image from being overlooked. Moreover, since a warning is given immediately after a defective image is captured, a time required is shorter than a conventional visual check by a radiographer. Therefore, a seriously ill patient does not need to hold a positioning so long. In addition, waiting time for the image judging process to be finished is short and it is not required to release a patient from positioning once. Therefore, positioning and imaging conditions only require minor adjustments even if a retake is needed, thus significantly reducing burdens on a radiographer and a patient.

Moreover, even in a preview image displayed on a small console with poor resolution and image quality, an area to be confirmed is highlighted or enlarged on the preview screen. Therefore, it becomes easier to confirm an image, and time and workload required for the confirmation can be greatly reduced.

Once a retake is instructed from the input part in console 5P, the preview image to be processed and a corresponding medical image are deleted from the storage section 52. When a retake is not instructed, correction processing and image processing may be executed on a medical image and the medical image may be displayed and transmitted to the server device 10 by the console 5. Alternatively, image data of the medical image may be transferred to the console 5P or the like, and correction processing and image processing may be executed on the medical image or the like, and then the medical image may be transmitted to the server device 10 by the console 5.

As described so far, according to the medical imaging system 100, a medical image which is a still image, and a preview image which is obtained by reducing the medical image are generated as the FPD 9 captures a certain part of a human body as a subject, and transmitted to the imaging console 5. The controlling section 51 of the imaging console 5 analyzes the preview image and judges whether the captured medical image meets predetermined criteria for a diagnostic medical image. When it is judged that the medical image does not meet the predetermined criteria for a diagnostic medical image, the controlling section 51 causes the display section 54 to display a warning.

Therefore, when a defective image which does not meet the predetermined criteria for a diagnostic medical image is picked up, a warning is provided immediately after the image is captured. Therefore, a radiographer is able to instantaneously recognize a defective image which is not suitable for a diagnostic use, thus preventing a defective image from being overlooked. Further, since a patient needs to hold positioning only for a short period of time, a burden on the patient can be reduced.

Specifically speaking, it becomes possible to make at least one of the judgments whether a captured medical image includes a missing portion in a specific region, whether a captured medical image includes any motion in a subject, whether a medical image was captured with a radiation dose which exceeds a predetermined reference level, and whether a captured medical image is processed under appropriate image processing conditions.

It should be noted that the second embodiment described above is one of preferred examples of the present invention, and the present invention is not limited thereto.

For example, in the foregoing embodiment, reduction of a medical image was performed on the FPD side. However, a medical image may be reduced on the side of the imaging console 5.

Further, in the second embodiment described above, the radiation source 3 is activated by an instruction from the operating station 6. However, the radiation source 3 may be activated by an instruction from the imaging console 5. The image readout conditions of the FPD 9 may be inputted from the imaging console 5.

Furthermore, in the foregoing second embodiment, the medical imaging system for generating a medical image by using the FPD was explained as an example. However, a unit for generating a medical image is not limited to the FPD, and CR may be used, for example.

Still further, in the foregoing second embodiment, as the outputting unit which outputs a warning (a judgment result) when it is judged that the captured medical image does not satisfy the criteria as the medical image for diagnosis (for example, when it is judged that there are motions in the subject), the display section 54 was explained as an example to output and display such warning. However, the warning may alternatively be outputted by a sound outputting apparatus, and the like.

Yet further, the medical imaging system 100 may have both of the configurations described in the first embodiment and the second embodiment. Namely, the medical imaging system 100 may have a system configuration which is enabled to execute the motion judging process using a medical image and display the judgment result (warning), as well as execute the image judging process (for example, the motion judging process B) by using a preview image and display the judgment result (warning). In addition, the medical imaging system 100 may have such a configuration that a user is able to set from the inputting section 53 whether the motion judgment using a medical image will be executed or the image judging process using a preview image will be executed.

Moreover, the above description disclosed an exemplary case where a HDD, a semiconductor non-volatile memory or the like is used as a computer-readable medium for the programs according to the present invention. However, the computer-readable medium is not limited thereto. As other computer-readable medium, a portable storage medium such as a CD-ROM may be applied. Also, carrier wave is applicable as a medium which provides data of the programs according to the present invention through a communication line.

More detail constituents and operations of each device in the medical imaging system may be changed as appropriate without departing from the spirit and scope of the present invention.

What is claimed is:

1. A medical imaging system, comprising:
an image generating unit which captures a front chest image of a subject and generates a front chest medical image which is a still image;
a region extracting unit which extracts a lung field region from the front chest medical image, divides the lung field region into a plurality of small regions, extracts high spatial frequency components with a high-pass filter for each of the plurality of small regions of the lung field region, calculates a maximum value or an integral value of response of the extracted high spatial frequency components in a range between Nyquist frequency fN and (fN−Δf), wherein Δf represents a predetermined value, compares either the calculated maximum value or the calculated integral value to a threshold value predetermined for the maximum value or to a threshold value predetermined for the integral value, and extracts, from the plurality of small regions, small regions having the threshold value or smaller as a plurality of local regions which include no edge of a rib bone;
a motion judging unit which extracts high spatial frequency components from each of the plurality of local regions extracted by the region extracting unit, calculates a motion feature value based on the extracted high spatial frequency components of the extracted plurality of local regions, and judges whether there is any motion in the subject during image capture based on the calculated motion feature value; and
a controlling unit which causes an outputting unit to output a judgment result made by the motion judging unit.

2. The medical imaging system according to claim 1, wherein the motion judging unit extracts high spatial frequency components for a plurality of directions and judges whether there is any motion in the subject during image capture based on the extracted high spatial frequency components for the plurality of directions.

3. The medical imaging system according to claim 1, further comprising:
a preview image generating unit which generates a preview image by reducing the medical image; and
a display unit which displays the preview image, wherein the region extracting unit extracts a subject region from the preview image and extracts the local region which includes no edge from the subject region, wherein
the motion judging unit extracts high spatial frequency components from the local region extracted from the preview image, and judges whether there is any motion in the subject in the medical image based on the extracted high spatial frequency components, and wherein the controlling unit causes the display unit to display a warning when it is judged by the motion judging unit that there is a motion in the subject in the medical image.

4. The medical imaging system according to claim 1, further comprising:
a preview image generating unit which generates a preview image by reducing the medical image;
a display unit which displays the preview image; and
an image processing unit which executes image processing on the preview image, wherein
the region extracting unit extracts a subject region from a preview image which has been undergone the image processing executed by the image processing unit and extracts the local region which includes no edge from the subject region, wherein
the motion judging unit extracts high spatial frequency components from the local region extracted from the preview image which has been undergone the image processing executed by the image processing unit, and judges whether there is any motion in the subject in the medical image based on the extracted high spatial frequency components, and wherein
the controlling unit causes the display unit to display a warning when it is judged by the motion judging unit that there is a motion in the subject in the medical image.

5. The medical imaging system according to claim 1, wherein the motion judging unit calculates the motion feature value on a basis of responses for respective directions of each of the plurality of local regions.

6. The medical image system according to claim 5, wherein the motion judging unit calculates average value for respective direction with regard to the responses for the respective directions of each of the respective local regions, calculates a difference between the calculated average values for the respective directions, and sets an absolute value of the difference as the motion feature value.

7. The medical imaging system according to claim 6, wherein
with respect to a vertical direction, a horizontal direction and two oblique directions, the motion judging unit calculates the average values,
the motion judging unit compares an absolute value of a difference value of the average values for the vertical direction and the horizontal direction with an absolute value of a difference value of the average values for the two oblique directions; and
the motion judging unit sets a larger value as the motion feature value.

8. A medical image processing apparatus comprising:
a computer processor comprising:
a region extracting unit structured to extract a lung field region from a front chest medical image which is a still image obtained by imaging a subject, to divide the lung field region into a plurality of small regions, to extract high spatial frequency components with a high-pass filter for each of the plurality of small regions of the lung field region, to calculate a maximum value or an integral value of response of the extracted high spatial frequency components in a range between Nyquist frequency fN and (fN−Δf), wherein Δf represents a predetermined value, to compare either the calculated maximum value or the calculated integral value to a threshold value predetermined for the maximum value or to a threshold value predetermined for the integral value, and to extract, from the plurality of small regions, small regions having the threshold value or smaller as a plurality of local regions which include no edge of a rib bone;
a motion judging unit structured to extract high spatial frequency components from the plurality of local regions extracted by the region extracting unit, to calculate a motion feature value based on the extracted high spatial frequency components of the extracted plurality of local regions, and to judge whether there is motion in the subject during image capture based on the calculated motion feature value; and
a controlling unit structured to cause an outputting unit to output a judgment result made by the motion judging unit.

9. A non-transitory computer-readable medium including computer readable instructions that, when executed by a computer, cause the computer to perform:
extracting a lung field region from a front chest medical image which is a still image obtained by imaging a subject, dividing the lung field region into a plurality of small regions, extracting high spatial frequency components with a high-pass filter for each of the plurality of small regions of the lung field region, calculating a maximum value or an integral value of response of the extracted high spatial frequency components in a range between Nyquist frequency fN and (fN−Δf), wherein Δf represents a predetermined value, comparing either the calculated maximum value or the calculated integral value to a threshold value predetermined for the maximum value or to a threshold value predetermined for the integral value, and extracting, from the plurality of small regions, small regions having the threshold value or smaller as a plurality of local regions which include no edge of a rib bone;
extracting high spatial frequency components from the plurality of local regions, calculating a motion feature value based on the extracted high spatial frequency components of the extracted plurality of local regions, and judging whether there is motion in the subject during image capture based on the calculated motion feature value; and
outputting a judgment result made by judging whether there is a motion in the subject.

* * * * *